US008794013B2

(12) United States Patent
Zhou et al.

(10) Patent No.: US 8,794,013 B2
(45) Date of Patent: Aug. 5, 2014

(54) METHOD AND SYSTEM FOR NUCLEATION CONTROL IN A CONTROLLED RATE FREEZER (CRF)

(75) Inventors: Ying Zhou, Naperville, IL (US); Theodore H. Gasteyer, III, Naperville, IL (US); Nigel J. Grinter, Buffalo Grove, IL (US); Alan T. Cheng, Naperville, IL (US); Yeu-Chuan Simon Ho, Naperville, IL (US); Robert R. Sever, Arlington Heights, IL (US)

(73) Assignee: Praxair Technology, Inc., Danbury, CT (US)

( * ) Notice: Subject to any disclaimer, the term of this patent is extended or adjusted under 35 U.S.C. 154(b) by 564 days.

(21) Appl. No.: 13/097,724

(22) Filed: Apr. 29, 2011

(65) Prior Publication Data
US 2012/0102982 A1   May 3, 2012

Related U.S. Application Data

(63) Continuation-in-part of application No. 12/266,760, filed on Nov. 7, 2008, and a continuation-in-part of
(Continued)

(51) Int. Cl.
| | |
|---|---|
| *F25D 25/00* | (2006.01) |
| *G01N 1/22* | (2006.01) |
| *C12M 3/00* | (2006.01) |
| *A01N 1/02* | (2006.01) |
| *F25D 3/10* | (2006.01) |
| *F25D 29/00* | (2006.01) |

(52) U.S. Cl.
CPC .............. *A01N 1/0289* (2013.01); *F25D 3/102* (2013.01); *A01N 1/0257* (2013.01); *F25D 29/001* (2013.01); *A01N 1/0284* (2013.01)
USPC ....... 62/62; 73/863.01; 73/863.11; 435/307.1

(58) Field of Classification Search
CPC .......... B01D 9/005; B01D 8/00; F04B 37/08; F04F 9/00; G01N 1/2258; G01N 1/22; F25D 3/10; A01N 1/02; A61B 10/0096
USPC ......................... 62/62, 66; 34/284; 424/184.1
See application file for complete search history.

(56) References Cited

U.S. PATENT DOCUMENTS

| | | | | |
|---|---|---|---|---|
| 4,397,158 A | * | 8/1983 | Brenik et al. | 62/380 |
| 4,481,780 A | * | 11/1984 | Delano | 62/46.1 |

(Continued)

FOREIGN PATENT DOCUMENTS

| | | |
|---|---|---|
| GB | 2 400 901 A | 10/2004 |
| WO | WO 2004/010780 A2 | 2/2004 |

(Continued)

OTHER PUBLICATIONS

J. M. Shaw and G.M. Jones; "Terminology Associated with Vitrification and Other Cryopreservation Procedures for Oocytes and Embryos"; Human Reproduction Update, vol. 9, No. 6, pp. 583-605, 2003.

*Primary Examiner* — Allen Flanigan
*Assistant Examiner* — Filip Zec
(74) *Attorney, Agent, or Firm* — Robert J. Hampsch

(57) ABSTRACT

A method and system for controlled rate freezing and nucleation of materials is provided. The presently disclosed system and method provides the ability to rapidly cool the materials contained in vials or other containers within a cooling unit via forced convective cooling using a laminar and uniform flow of cryogen in proximity to the plurality of vials disposed within the cooling unit. The rapid cooling of the biological materials is achieved by precisely controlling and adjusting the temperature of the cryogen being introduced to the system as a function of time. The presently disclosed methods to systems also provide nucleation control via temperature quench and depressurized nucleation control.

18 Claims, 11 Drawing Sheets

Related U.S. Application Data application No. 11/702,479, filed on Feb. 5, 2007, which is a continuation-in-part of application No. 11/702,472, filed on Feb. 5, 2007.

(60) Provisional application No. 60/986,814, filed on Nov. 9, 2007, provisional application No. 60/771,868, filed on Feb. 10, 2006.

(56) References Cited

U.S. PATENT DOCUMENTS

| | | | | |
|---|---|---|---|---|
| 4,739,622 A | * | 4/1988 | Smith | 62/78 |
| 4,792,302 A | * | 12/1988 | Baker et al. | 432/59 |
| 5,048,300 A | * | 9/1991 | Lihl | 62/48.1 |
| 6,387,322 B1 | * | 5/2002 | Gallus | 422/38 |
| 6,684,524 B1 | | 2/2004 | Sennhenn et al. | |
| 6,684,646 B2 | * | 2/2004 | Voute et al. | 62/66 |
| 2002/0031577 A1 | | 3/2002 | Arends et al. | |
| 2003/0219475 A1 | * | 11/2003 | Truong-Le | 424/450 |
| 2007/0186567 A1 | | 8/2007 | Gasteyer et al. | |

FOREIGN PATENT DOCUMENTS

| | | |
|---|---|---|
| WO | WO 2005/118785 A1 | 12/2005 |
| WO | WO 2009/062025 A2 | 5/2009 |

\* cited by examiner

METHOD AND SYSTEM FOR NUCLEATION CONTROL IN A CONTROLLED RATE FREEZER (CRF)

RELATED APPLICATIONS

The present application is a continuation in part of U.S. patent application Ser. No. 12/266,760 filed Nov. 7, 2008 which claims priority to U.S. provisional patent application No. 60/986,814 filed on Nov. 9, 2007. This application is also a continuation in part of U.S. patent application Ser. No. 11/702,472 filed Feb. 2, 2007 and Ser. No. 11/702,479 filed Feb. 2, 2007 both of which claim priority to U.S. provisional patent application No. 60/771,868 filed on Feb. 10, 2006. The disclosures of all of the above noted applications are incorporated by reference herein.

FIELD OF THE INVENTION

The present invention broadly relates to a cryopreservation process, and more particularly, to a method and system for providing controlled rate freezing and nucleation control of biological materials that minimize cell damage resulting from intercellular ice formation and solute effects that arise during the cryopreservation process.

BACKGROUND OF THE INVENTION

Cryopreservation is a process used to stabilize biological materials at very low temperatures. Previous attempts to freeze biological materials, such as living cells often results in a significant loss of cell viability and in some cases as much as 80% or more loss of cell activity and viability.

Cell damage during cryopreservation usually occurs as a result of intracellular ice formation within the living cell during the freezing step or during subsequent recrystallization. Rapid cooling often leads to formation of more intracellular ice since water molecules are not fully migrated out of the cell during the short timeframe associated with the rapid cool-down rates. Intercellular ice formation also can arise during recrystallization that occurs during the warming or thawing cycles. If too much water remains inside the living cell, damage due to initial ice crystal formation during the rapid cooling phase and subsequent recrystallization during warming phases can occur and such damage is usually lethal.

On the other hand, slow cooling profiles during cryopreservation often results in an increase in the solute effects where excess water is migrated out of the cells. Excess water migrating out of the cells adversely affects the cells due to an increase in osmotic imbalance. Thus, cell damage occurs as a result of osmotic imbalances which can be detrimental to cell survival and ultimately lead to cell damage and a loss of cell viability.

Current cryopreservation techniques involve using either conductive based cryogenic cooling equipment such as a cold shelf or lyophilizer type freezer unit or convective based cryogenic cooling equipment such as controlled rate freezers and cryo-cooler units. Such equipment, however, is only suitable for relatively small volume capacities and not suitable for commercial scale production and preservation of biological materials such as therapeutic cell lines. For example, the largest commercially available controlled rate freezer suitable for use with biological materials holds only about 8000 or so closely packed vials. One such system is the Kryo 1060-380 capable of storing 8000×2 ml ampoules. Such existing controlled rate freezers, including the Kryo 1060 series, also suffer from the non-uniformity in cooling vial to vial due, in part, to the non-uniform flow of cryogen within the freezers and the requirement for close packing of the vials within the freezer. The size of individual conventional freezers is limited due to these non-uniform effects. As conventional controlled rate freezers are scaled up in size the non-uniformities in cooling increase. Consequently, the size of conventional controlled rate freezers must be limited to prevent non-uniform sample-to-sample properties due to non-uniform cooling of each sample. The only effective way to further increase the quantity of samples processed at once using conventional controlled rate freezers is to use multiple controlled rate freezers.

Many conventional freezing systems utilize internal fans to disperse cryogen around the unit and deliver the refrigeration to the vials via convection. Such convection based cooling or freezing systems cannot achieve temperature uniformity as the vials are often located at various distances from the internal fan or packed in the shadow of other vials or trays. Vials of biological material exposed to high velocity turbulent flow of cryogen are typically cooled at a different rate and often much faster than vials situated further away from the fan.

There are also existing lyophilizer type of control rate freezers that can handle large volumes of vials but typically rely on thermal conduction between cold shelves in the lyophilizer unit and the vials. However, it is impossible to provide a uniform conductive surface area on the bottom of each glass vial since most glass vial bottoms are concave. Therefore, temperature variations during the freezing process from vial to vial are the biggest drawback for these types of equipment. Furthermore, the cooling rate can be painfully slow due to the very small conductive surface of the vial that remains in contact with the cold shelves.

Prior attempts to mitigate the loss of cell activity and viability involved the use of cryoprotective additives such as DSMO and glycerol. Use of such cryoprotectives during the cryopreservation process has demonstrated a reduction in cell losses attributable to the freezing and subsequent thawing cycles. However, many cryoprotectants such as DSMO are toxic to human cells and are otherwise not suitable for use in whole cell therapies. Disadvantageously, cryoprotectants also add a degree of complexity and associated cost to the cell production and preservation process. Also, cryoprotectants alone, have not eradicated the problem of loss of cell activity and viability.

Another problem associated with the above mentioned prior art systems is a lack of control with respect to the uniformity of the nucleation temperature between the multiple vials. This variability in the nucleation temperature of the multiple vials can lead to non-uniform vial-to-vial properties. Such properties can include cell activity and viability as well as the crystal structure of the frozen material and the time needed to complete a freeze drying process. Consequently, controlling the generally random process of nucleation in the freezing stage of a cryopreservation, lyophilization, or freeze-drying process to increase the product uniformity from vial-to-vial in the finished product would be highly desirable in the art.

In a typical pharmaceutical freeze-drying process, multiple vials containing a common aqueous solution are placed on shelves that are cooled, generally at a controlled rate, to low temperatures. The aqueous solution in each vial is cooled below the thermodynamic freezing temperature of the solution and remains in a sub-cooled metastable liquid state until nucleation occurs.

The range of nucleation temperatures across the vials is distributed randomly between a temperature near the thermodynamic freezing temperature and some value significantly (e.g., up to about 30° C.) lower than the thermodynamic freezing temperature. This distribution of nucleation temperatures causes vial-to-vial variation in ice crystal structure and ultimately the physical properties of the lyophilized product. Furthermore, the drying stage of the freeze-drying process must be excessively long to accommodate the range of ice crystal sizes and structures produced by the natural stochastic nucleation phenomenon.

Additives have been used to increase the nucleation temperature of sub-cooled solutions. These additives can take many forms. It is well known that certain bacteria (e.g., Pseudomonas syringae) synthesize proteins that help nucleate ice formation in sub-cooled aqueous solutions. Either the bacteria or their isolated proteins can be added to solutions to increase the nucleation temperature. Several inorganic additives also demonstrate a nucleating effect; the most common such additive is silver iodide, AgI. In general, any additive or contaminant has the potential to serve as a nucleating agent. For instance, lyophilization vials prepared in environments containing high particulate levels will generally nucleate and freeze at a lower degree of sub-cooling than vials prepared in low particulate environments.

All the nucleating agents described above are labeled "additives," because they change the composition of the medium in which they nucleate a phase transition. These additives are not typically acceptable or desirable for FDA regulated and approved freeze-dried pharmaceutical products. These additives also do not provide control over the time and temperature when the vials nucleate and freeze. Rather, the additives only operate to increase the average nucleation temperature of the vials.

Ice crystals can themselves act as nucleating agents for ice formation in sub-cooled aqueous solutions. In the "ice fog" method, a humid freeze-dryer is filled with a cold gas to produce a vapor suspension of small ice particles. The ice particles are transported into the vials and initiate nucleation when they contact the fluid interface.

The "ice fog" method does not control the nucleation of multiple vials simultaneously at a controlled time and temperature. In other words, the nucleation event does not occur concurrently or instantaneously within all vials upon introduction of the cold vapor into the freeze-dryer. The ice crystals will take some time to work their way into each of the vials to initiate nucleation, and transport times are likely to be different for vials in different locations within the freeze-dryer. For large scale industrial freeze-dryers, implementation of the "ice fog" method would require system design changes as internal convection devices may be required to assist a more uniform distribution of the "ice fog" throughout the freeze-dryer. When the freeze-dryer shelves are continually cooled, the time difference between when the first vial freezes and the last vial freezes creates a difference in the temperature between vials, which will also increase the vial-to-vial non-uniformity in the final freeze-dried products.

Vial pre-treatment by scoring, scratching, or roughening has also been used to lower the degree of sub-cooling required for nucleation. As with the other prior art methods, vial pre-treatment also does not impart any degree of control over the time and temperature when the individual vials nucleate and freeze, but instead only increases the average nucleation temperature of all vials.

Vibration has also been used to nucleate a phase transition in a metastable material. Vibration sufficient to induce nucleation occurs at frequencies above 10 kHz and can be produced using a variety of equipment. Often vibrations in this frequency range are termed "ultrasonic," although frequencies in the range 10 kHz to 20 kHz are typically within the audible range of humans. Ultrasonic vibration often produces cavitation, or the formation of small gas bubbles, in a sub-cooled solution. In the transient or inertial cavitation regime, the gas bubbles rapidly grow and collapse, causing very high localized pressure and temperature fluctuations. The ability of ultrasonic vibration to induce nucleation in a metastable material is often attributed to the disturbances caused by transient cavitation. The other cavitation regime, termed stable or non-inertial, is characterized by bubbles that exhibit stable volume or shape oscillations without collapse. U.S. Patent Application 20020031577 A1 discloses that ultrasonic vibration can induce nucleation even in the stable cavitation regime, but no explanation of the phenomenon is offered. GB Patent Application 2400901A also discloses that the likelihood of causing cavitation, and hence nucleation, in a solution using vibrations with frequencies above 10 kHz may be increased by reducing the ambient pressure around the solution or dissolving a volatile fluid in the solution.

An electrofreezing method has also been used in the past to induce nucleation in sub-cooled liquids. Electrofreezing is generally accomplished by delivering relatively high electric fields (1 V/nm) in a continuous or pulsed manner between narrowly spaced electrodes immersed in a sub-cooled liquid or solution. Drawbacks associated with an electrofreezing process in typical lyophilization applications include the relative complexity and cost to implement and maintain, particularly for lyophilization applications using multiple vials or containers. Also, electrofreezing cannot be directly applied to solutions containing ionic species (e.g., NaCl).

Recently, there have been studies that examined the concept of 'vacuum-induced surface freezing' (See e.g., U.S. Pat. No. 6,684,524). In such 'vacuum induced surface freezing', vials containing an aqueous solution are loaded on a temperature controlled shelf in a freeze-dryer and held initially at about 10 degrees Celsius. The freeze-drying chamber is then evacuated to near vacuum pressure (e.g., 1 mbar) which causes surface freezing of the aqueous solutions to depths of a few millimeters. Subsequent release of vacuum and decrease of shelf temperature below the solution freezing point allows growth of ice crystals from the pre-frozen surface layer through the remainder of the solution. A major drawback for implementing this 'vacuum induced surface freezing' process in a typical lyophilization application is the high risk of violently boiling or out-gassing the solution under stated conditions.

Improved control of the nucleation process could enable the freezing of all unfrozen solution containers in a cryogenic chiller or freeze-dryer to occur within a narrower temperature and time range, thereby yielding a product with greater uniformity from sample-to-sample. With regards to freeze-drying systems, controlling the minimum nucleation temperature affects the ice crystal structure formed within the vial and allows for a greatly accelerated freeze-drying process.

In view of the above, what is needed is a method and system to control the uniformity of the temperature profiles and nucleation temperatures of the multiple containers so as to provide a more uniform finished product sample-to-sample. Moreover, the system and method should be both efficient and readily scalable to handle commercial scale production.

SUMMARY OF THE INVENTION

The inventors have recognized and appreciated a need for delivering temperature adjusted cryogenic cold gas for uniformly cooling and freezing material in a plurality of containers during a cryopreservation process. Furthermore, the inventor has recognized and appreciated that it is possible to provide a more uniform freezing process for each container by controlling the nucleation of freezing. More generally, the inventor has recognized the advantages of a device and method capable of controlling nucleation of freezing by either pressure induced or temperature quench induced nucleation control useful in such a freezing processes. Such a device and method is capable of being used for any number of different applications besides cryopreservation.

In an exemplary embodiment, a method of controlling a freezing process of material in a plurality of containers includes providing a plurality of containers each holding a material in a cooling chamber. The method includes uniformly cooling the material in each of the plurality of containers to a temperature near or below a phase transition temperature of the material in each of the plurality of containers while the containers are in the cooling chamber. The method further includes uniformly performing a temperature quench of the material in each of the plurality of containers to initiate and control nucleation of freezing of the material in each of the plurality of containers.

In one exemplary embodiment, the uniformity of the container temperatures are maintained within ±2.5° C. of each other during the freezing process, prior to nucleation, regardless of a location in the cooling chamber where the material is frozen. After nucleation, the uniformity of the container temperatures may be maintained within ±5° C. of each other during the remainder of the freezing process regardless of a location in the cooling chamber where the material is frozen. In another exemplary embodiment, the uniformity of the container temperatures are maintained within ±1° C. of each other during the freezing process, prior to nucleation, regardless of a location in the cooling chamber where the material is frozen. The above example of temperature uniformity should not be construed as limiting with regards to the current disclosure. Other possible temperature ranges may be used during a freezing process.

In a further exemplary embodiment, the freezing process results in substantially simultaneous freezing of the material in all of the containers regardless of a location in the cooling chamber where the material is frozen.

In an additional exemplary embodiment, a method of controlling a freezing process of material in a plurality of containers includes providing a plurality of containers each holding a material in a cooling chamber. The method includes uniformly cooling the material in each of the plurality of containers to a temperature near or below a phase transition temperature of the material in each of the plurality of containers while the containers are in the cooling chamber. The method further includes decreasing a pressure applied to the material in each of the plurality of containers to initiate and control nucleation of freezing of the material in each of the plurality of containers.

In a further exemplary embodiment, a cryogenic chiller or freezing system includes a cooling chamber adapted to hold a plurality of containers. The cryogenic chiller or freezing system also includes an intake circuit adapted to provide a uniform flow and temperature of a cryogenic cold gas to each of the plurality of containers. Heat is transferred between the plurality of containers and the cryogenic cold gas. The cryogenic chiller or freezing systems further includes a pressure control adapted to decrease a pressure applied to each of the plurality of containers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

The foregoing and other aspects, embodiments, and features of the present teachings can be more fully understood from the following description in conjunction with the accompanying drawings.

BRIEF DESCRIPTION OF THE DRAWINGS

The accompanying drawings are not intended to be drawn to scale. For purposes of clarity, not every component may be labeled in every drawing. In the drawings.

DETAILED DESCRIPTION OF THE INVENTION

Figure 1:
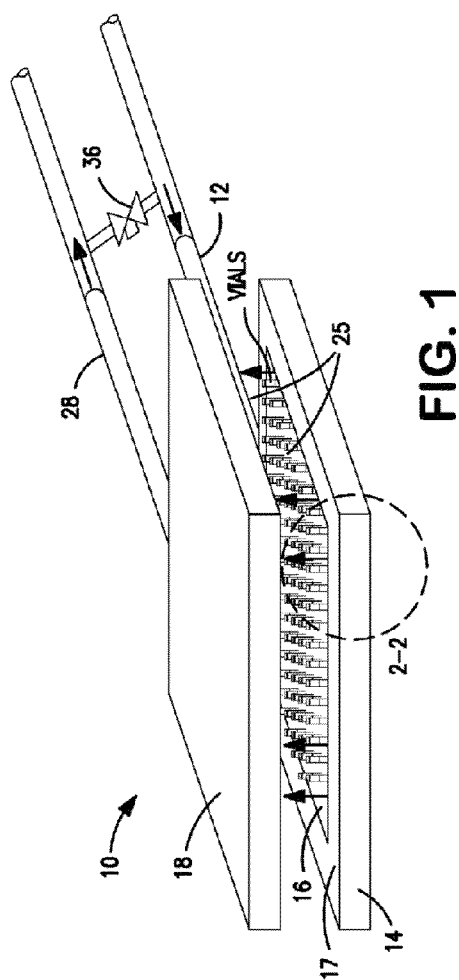
FIG. 1 is a schematic illustration of an embodiment of a uniform flow cryogenic chiller unit.

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. It should be appreciated, then, that the various concepts and embodiments introduced above and those discussed in greater detail below may be implemented in any of numerous ways, as the disclosed concepts and embodiments are not limited to any particular manner of implementation. In addition, it should be understood that aspects of the invention may be used alone or in any suitable combination with other aspects of the invention.

Controlled Rate Freezer

Cryopreservation of biological materials typically involves rapid cooling of biological specimens from temperatures of 40° C. or more to temperatures of about −100° C. or lower. The specified temperatures, cool-down rates, and cooling profiles, expressed as temperature of the materials as a function of time, are highly dependent on the specific biological materials to be frozen. In most cryopreservation of biological materials, the freezing process must be precisely controlled. Uniformity in temperatures, cool-down rates, and cooling profiles from container to container and batch to batch is of utmost importance in the production process.

The presently disclosed method and system represents an improvement to current cryopreservation processes for biological materials. The presently disclosed system and method provides the ability to rapidly cool the biological materials contained in vials or other containers within a cooling unit primarily via forced convective cooling using a laminar and uniform flow of cryogen in proximity to each of the plurality of vials disposed within the cooling unit. In addition, the present system and method are capable of providing the rapid cooling of the biological materials over a wide range of cooling rates and also hold the temperature of the biological materials at any prescribed temperature where specified.

More specifically, the rapid cooling of the biological materials is achieved by precisely controlling and adjusting the temperature of the cryogen being introduced to the system as a function of time. In one mode, the disclosed embodiments of the system are adapted to provide a stepwise or quick drop in cryogen temperature 102 (See FIG. 6) to generate a higher degree of sub-cooling within the sample materials 100 thereby minimizing the exothermic effects of the phase transition (e.g. water-to-ice transformation) in the vials. In another mode, the disclosed embodiments of the present controlled rate freezing or cryogenic chilling system and method are adapted to provide a ramp down of cryogen cold gas temperature of about −4.5° C. per minute 112 (See FIG. 7) and of about −5.0° C. per minute (See FIG. 8) to provide rapid cooling of the sample biological materials 110, 120 yet minimize any vial to vial variations in temperature.

Temperatures of the cold cryogen gas introduced to the cooling chamber or unit are adjusted or otherwise controlled by mixing a source of liquid nitrogen with a source of warmer nitrogen gas just prior to introduction of the cold cryogen gas to the cooling unit. The mixed flow is then introduced and dispersed throughout the cooling unit by means of suitable cryogen intake circuits, as described herein. The warmer nitrogen gas is preferably either room temperature nitrogen gas from a supply source or nitrogen gas exiting from the cooling unit and recycled to the cryogen intake circuit. The warmer nitrogen gas mixed with the cold nitrogen liquid or gas also acts as a motive gas and preferably has a volumetric flow rate many times that of the liquid or cold nitrogen.

Through the appropriate mixing of the warmer nitrogen gas with the cooler nitrogen flow, the present system creates a laminar and uniform flow of the cryogen across the entire cooling area targeted by the cold cryogen gas. By recycling the nitrogen gas exiting the cooling unit(s), the presently disclosed system and method also offers a higher utilization efficiency of the cryogen (e.g. nitrogen) than existing controlled rate freezers.

Given the uniform flow of the cold cryogen gas across all samples or vials of the biological material, it has been found that precise control of the cold cryogen gas temperature and cryogen temperature gradient has a direct correlation to the observed cooling rates of the biological material within the cooling unit, for a given biological material. For example, when the cold cryogen gas temperature provided to the present cooling unit is varied or ramped at about −4.5° C./min to about −5.0° C./min, an average cooling rate of the biological material of approximately −2.5° C./min is achieved with minimum vial-to-vial temperature variations. (See FIGS. 7 and 8).

Figure 2:
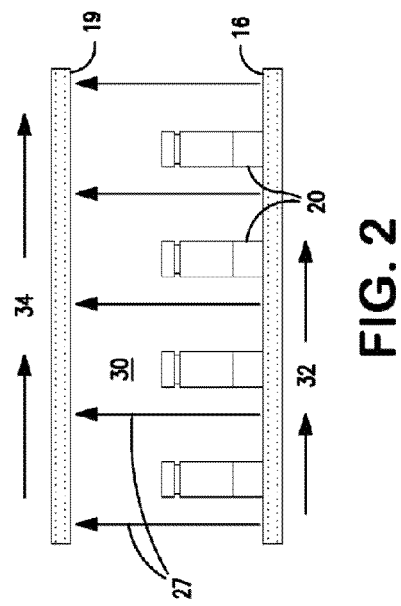
FIG. 2 is a detailed view of a cut-away portion of the uniform flow cryogenic chiller unit of FIG. 1 depicting the uniform flow characteristics of the cryogen gas proximate the vials of biological materials.

Turning now to FIGS. 1 and 2, there are depicted selected views of a cooling unit, referred to as a uniform flow cryogenic chiller 10. As seen therein, the uniform flow cryogenic chiller 10 includes a cryogen intake circuit 12 or conduit coupled to a source of cryogen (not shown). The uniform flow cryogenic chiller 10 further includes a base gas injection box 14, a porous metal plate 16 disposed or set in or near the top surface 17 of the gas injection box 14, and a corresponding gas removal box 18 positioned immediately above the base gas injection box 14 and a porous metal plate 19 disposed therein. Alternatively, various arrangements of supported polymeric membranes suitable to withstand the cryogenic temperatures or other perforated plates with mechanically punctured or chemically etched holes can be used in lieu of the porous metal plates.

The porous metal plate 16 associated with the gas injection box 14 is adapted to receive and hold a plurality of vials 20 containing biological materials. Also disposed in or near the vials 20 is a plurality of temperature sensors 25 to be used as inputs to the system controller (not shown). The cryogen intake circuit 12 or conduit is further coupled to the gas injection box 14 that is adapted to receive the cryogen intake flow and evenly distribute the cryogen across the porous metal plate 16. The cold cryogen gas flows in a uniform manner into an intake plenum 32 in the gas injection box 14 through the lower porous metal plate 16 holding the vials 20 into the cooling space 30 and then to the gas removal box 18 which also includes an upper porous metal plate 19 and an exhaust manifold 34. From the exhaust manifold 34, the spent nitrogen gas exits via the gas exhaust circuit 28 or conduit.

As discussed above, the cooling of the vials 20 is provided by the heat transfer between the vials 20 and the cryogenic cold gas 27 flowing through the cooling area 30. The cryogenic cold gas 27 is produced in the cryogen intake circuit 12 by mixing liquid nitrogen with a warmer nitrogen gas or recirculating spent nitrogen gas from the gas exhaust circuit 28 with appropriate mixing apparatus or valves 36. The vials 20 are cooled generally at a slightly slower rate than the cryogenic cold gas. The temperature difference between the vials 20 and the cryogenic cold gas 27 is the thermal driving force to cool down the vials 20. Therefore, it is possible to freeze the vials 20 with any temperature profile by precisely controlling the temperature of the cryogenic cold gas 27 at a particular temperature profile.

Preferably, the cryogenic cold gas temperature, and more particularly, the temperature profile is actively controlled in response to the average temperatures indicated by the temperature or thermal sensors 25 disposed at or near the vials 20. In the present embodiment, the average temperatures in a plurality of vials 20 are being used as the inputs for the active control of the system. Preferably, a cascade based control methodology where the system temperatures including vial temperatures are monitored and controlled by a primary system controller, which transfers set point signals and other commands to a slave controller responsible for modulating the cryogenic cold gas temperatures in the intake circuit. As discussed in more detail below, the cryogenic cold gas temperature profile is created through the operative control of a mixing valve that blends a specified volume of cold liquid nitrogen with a specified volume of warmer nitrogen gas. The blending or mixing is preferably a continuous operation that changes as a function of time to yield a cryogenic cold gas having a temperature that follows a prescribed temperature profile (i.e. temperature that changes as a function of time). In short, operative temperature control of the uniform flow cryogenic chiller is achieved by controlling the temperature profile of the cryogenic cold gas in the intake circuits. As discussed above, it has been found that precise control of the cryogenic cold gas temperatures and temperature gradients has a direct correlation to the observed cooling rates of the given biological material.

As the cryogenic cold gas enters the lower gas injection box 14, the cryogenic cold gas 27 is dispersed into an intake plenum 32 through a series of downward oriented sparger pipes or channels within the gas injection box (not shown). This dispersion in the intake plenum 32 promotes an even distribution of the cryogenic cold gas 27 across the entire surface of the porous metal plate 16. The downward oriented distribution of cryogenic cold gas 27 in the intake plenum 32 avoids the direct impingement of the cryogenic cold gas 27 on the porous metal plate 16, resulting in cold spots and non-uniform cooling. The porous metal plate 16 in the gas injection box 14 forces the cryogenic cold gas 27 to distribute uniformly across the entire cooling area 30 of the uniform flow cryogenic chiller 10, where the vials or other containers of biological material are held. The spent nitrogen is collected in an exhaust manifold 34 disposed above the porous plate 19 in the gas removal box 18. As illustrated, the cryogenic cold gas 27 has only a short path to traverse from the intake plenum 32 through the porous plate 16 upward into the cooling area 30, through the upper porous plate 19 and into the exhaust manifold 34. The uniform direction and short distance of the cryogenic cold gas flow results in a high level of uniformity in vial 20 cooling within the cryogenic chiller 10. Pore sizes for the porous metallic plates 16, 19 are preferably on the order of about 2 to 50 microns in diameter, as small pores enhance the dispersion and resulting uniformity in cooling. By cooling or freezing the biological material at the optimized rate, the survival rate of the cells is enhanced yielding potentially higher drug potency.

At the freezing point of the solutions, the heat of crystallization keeps the solution temperature from dropping, and sometimes the temperature within the vial can also rise. Using one or more thermal or temperature sensors 25 embedded in or near selected control vials, the temperature of cryogenic cold gas can be adjusted to minimize temperature deviation from the optimized cooling rate, as needed. In other words, control of the system may be either pre-programmed or may be a real-time feedback based operation.

Pharmaceutical, biopharmaceutical or biologic solutions contained in vials or containers for cryopreservation would benefit from the present system and methods. Such biological or biopharmaceutical materials may include microorganisms, tissues, organs, stem cells, primary cells, established cell lines, small multicellular organisms, complex cellular structures such as embryos, or a solution or mixture that includes: live or attenuated viruses; nucleic acids; monoclonal antibodies; polyclonal antibodies; biomolecules; nonpeptide analogues; peptides, proteins, including fusion and modified proteins; RNA, DNA and subclasses thereof, oligonucleotides; viral particles; and similar such materials or components thereof. Also, the containers used for holding the biological materials may include vials, straws, polymeric bags, or other form of suitable container.

Figure 3:
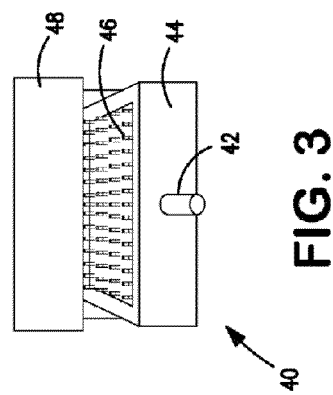
FIG. 3 is a picture of an embodiment of a single batch uniform flow cryogenic chiller unit.
Figure 4:
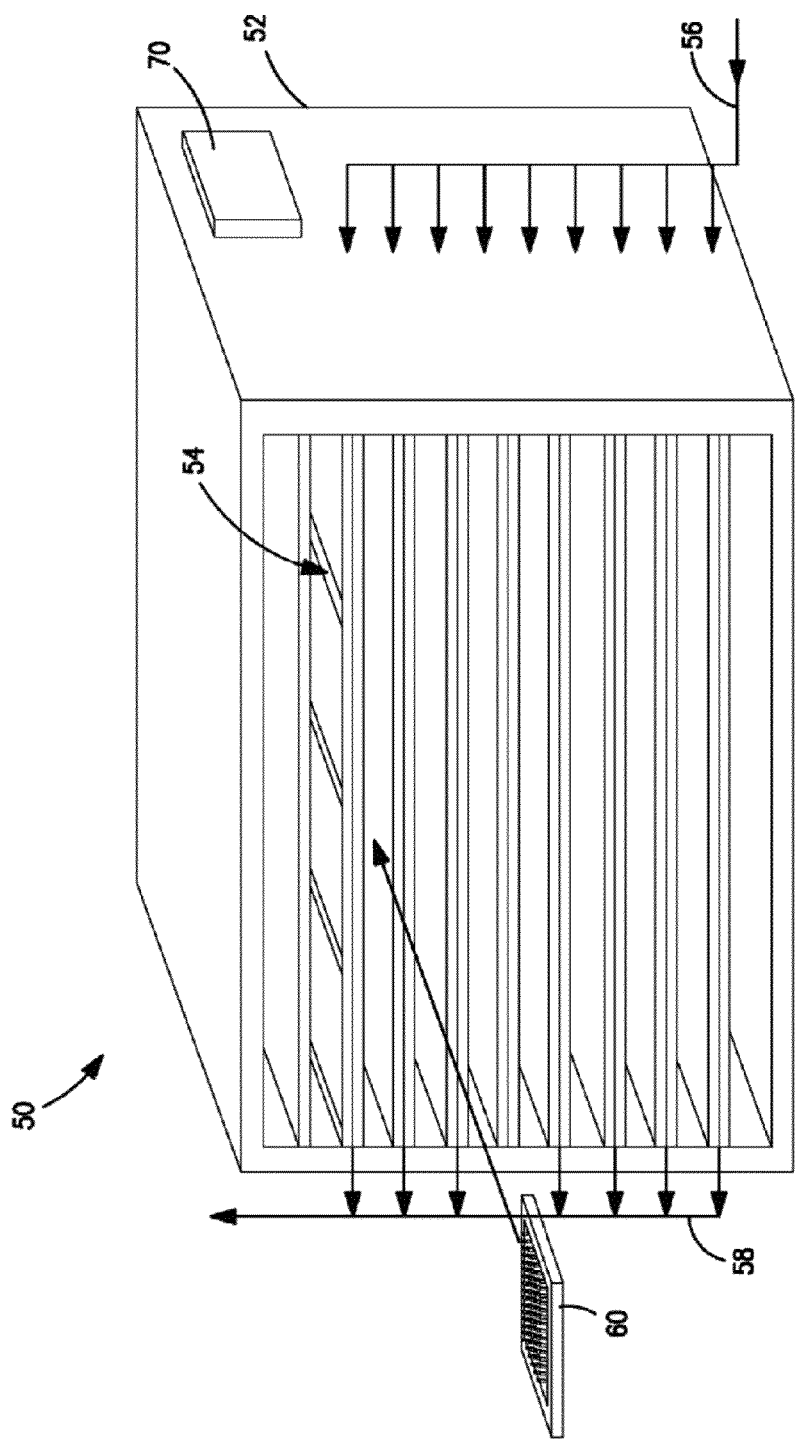
FIG. 4 is a schematic view of an embodiment of a multi-batch or large commercial scale uniform flow cooling chamber.
Figure 5:
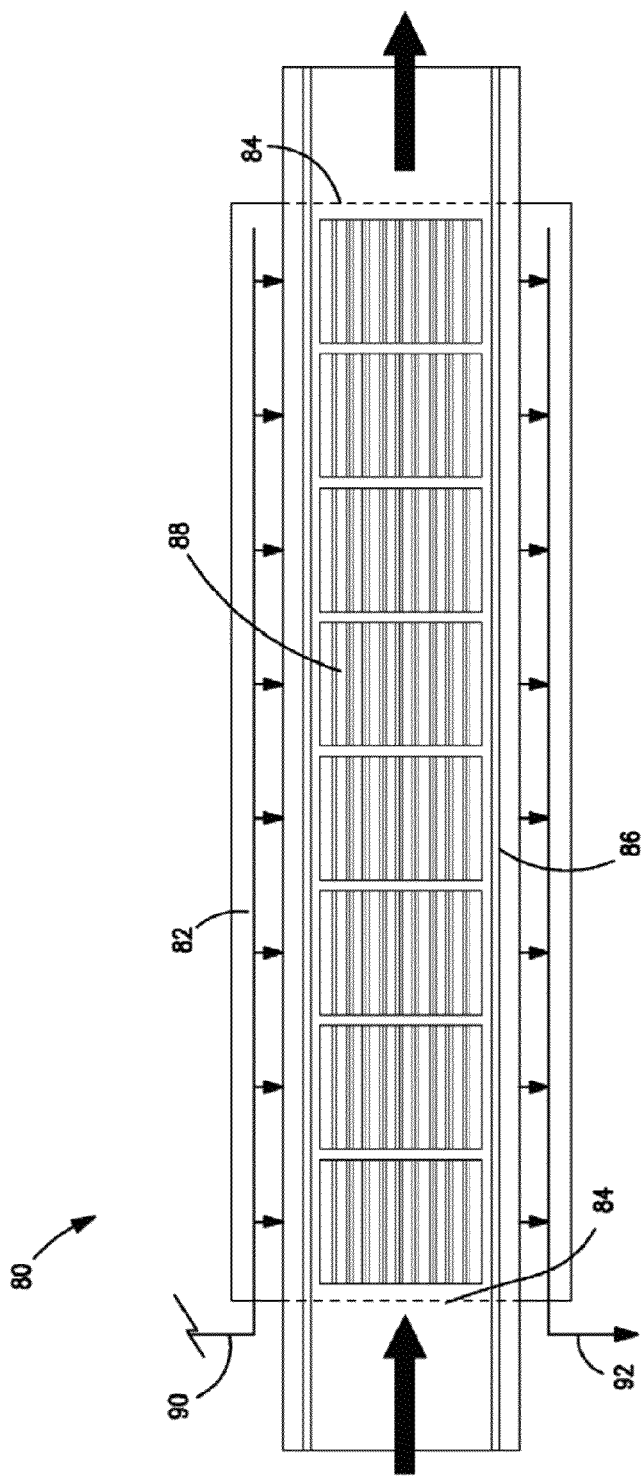
FIG. 5 is a schematic view of another embodiment of a continuous type uniform flow cooling unit.

FIGS. 3, 4, and 5 depict various embodiments of the present uniform flow controlled rate freezer or cryogenic chiller incorporating the uniform flow approach or concept. More specifically, FIG. 3 is a picture of a single modular unit 40 of the controlled rate freezer adapted to hold one of the uniform flow cryogenic chillers. The external housing for the unit 40 pictured in FIG. 3 is solid stainless steel housing with a gas injection box 44 having an intake conduit 42, a plenum, and porous plate 46 as well as a gas removal box 48 having a porous plate, an exhaust manifold, and an exhaust conduit. The pictured unit is dimensioned to hold a single laminar and uniform flow cryogenic chiller as described above with reference to FIGS. 1 and 2.

FIG. 4 depicts a multi batch or commercial scale unit 50 that includes a cooling chamber 52 that includes a plurality of shelves or rails 54 adapted to hold multiple uniform flow cryogenic chiller assemblies. Such multi-batch or commercial scale unit 50 is preferably capable of cryopreserving 50,000 or more vials or other such containers per production run. As seen in FIG. 4, the cryogen intake circuit 56 and spent gas exhaust circuit 58 are designed and sized to circulate sufficient cryogen to the multiple individual cryogenic chillers 60. Control system 70 is used to operatively control the temperature profile of the cold cryogen gas provided to each shelf 54, or to each cryogenic chiller assembly 60 depending on the inputs from the thermal sensors disposed within the system.

FIG. 5 depicts yet another possible commercial scale embodiment of the controlled rate freezer or chiller system 80 that operates in a continuous or conveyorized manner. Again, the unit 80 and cryogenic cold gas intake circuit 90 and gas exhaust circuit 92 are designed and sized to circulate sufficient cryogenic cold gas to individualized containers or tray assemblies 88 disposed along a conveyor 86 within the tunnel-type freezer chamber 82 having an entrance and exit means 84. In this continuous operation, the cooling profiles of different containers, vials or trays could be either time based, as described above with regard to the batch systems, or spatially based (e.g. spatial location within the chamber).

The ability to precisely control the cooling rate of biological material provides many benefits. For example, biological material frozen in an aqueous solution may experience various stresses during the freezing and subsequent thawing process that may impair the function or activity of the material. Ice formation may physically disrupt the material or create severe changes in the interfacial bonding, osmotic forces, solute concentrations, etc. experienced by the material. Proper design of the freezing process can mitigate such stresses and the present system and method allows for the precise control of the freezing process to achieve uniformity in the frozen material in all vials in accordance with the designed freezing profile.

One exemplary system includes a cryogen source, an intake circuit coupled to the cryogen source and adapted for providing a uniform flow and temperature of a cryogenic cold gas to a cooling chamber, an exhaust circuit and a control system. The cooling chamber comprises an intake plenum, an exhaust manifold, and two or more parallel porous surfaces that define a cooling area between adjacent parallel surfaces with one of the parallel porous surfaces disposed adjacent to the intake plenum and in fluid communication with the intake plenum and another of the parallel porous surfaces disposed adjacent to the exhaust manifold, the parallel porous surfaces and cooling area adapted to retain, or hold, a plurality of containers of biological materials. The exhaust circuit of the freezing or chilling system is adapted to remove the cryogen gas from the exhaust manifold of the cooling chamber whereas the control system is adapted to adjust the flow rates of the cryogen source in the intake circuit and any cryogen gas in the exhaust circuit to adjust the temperature of the cold cryogen gas delivered to the cooling chamber in response to a desired cooling rate of the biological materials and measured temperatures within the cooling chamber. In this manner, a uniform, unidirectional, and laminar flow of temperature adjusted cryogenic cold gas is delivered to the cooling area between the parallel porous surfaces and parallel to each of the plurality of containers to uniformly cool the biological materials.

The operation of the above disclosed exemplary system includes the steps of: (i) placing a plurality of containers of the biological materials in a cooling area defined as the area between parallel porous surfaces within a cooling chamber; (ii) mixing a liquid cryogen with a warmer gas to produce a cold cryogenic gas at a selected temperature profile, the temperature profile corresponding to a desired cooling rate of the biological materials within the containers; (iii) delivering a unidirectional, laminar flow of the temperature adjusted cryogenic cold gas through one of the porous surfaces to the cooling area between the parallel porous surfaces and parallel to each of the plurality of containers to uniformly cool the biological materials; and (iv) promptly exhausting the gas from cooling chamber via another parallel porous surface so as to prevent recirculation of the gas within the cooling area.

Figure 9:
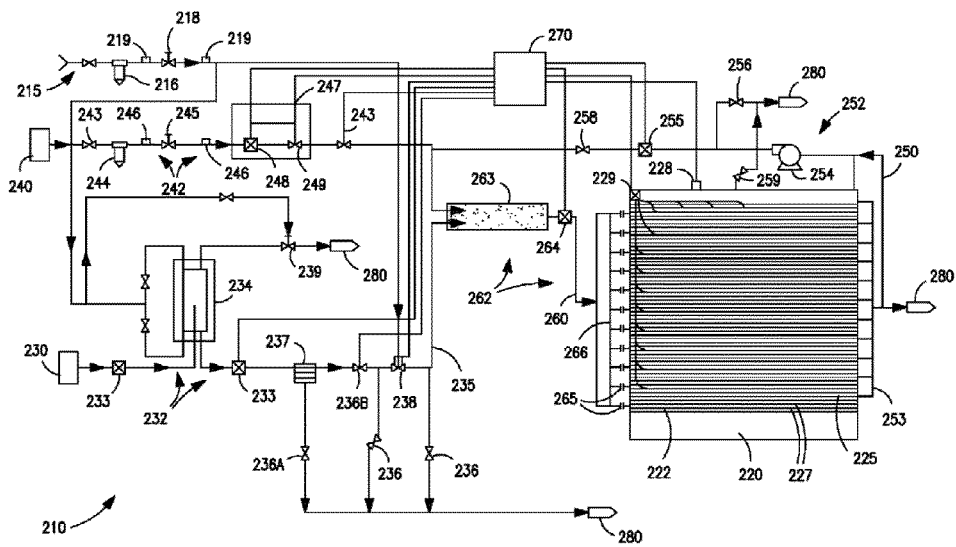
FIG. 9 depicts an embodiment of a multi-batch or commercial scale uniform flow cooling system with more detailed views of the process and instrumentation.

Turning now to FIG. 9, a detailed embodiment is presented. The illustrated cryogenic chiller system 210 includes a cooling chamber 220 adapted to receive a cryogenic cold gas 260 from a cryogen cold gas circuit 262, a source of liquid nitrogen 230, a liquid supply circuit 232 including a phase separator 234, a supply of gaseous nitrogen 240, a gas supply circuit 242, a recirculating cryogenic gas 250 and a gas recirculation circuit 252. The cryogenic chiller system 210 further includes a programmable logic controller (PLC) based control system 270 that operatively controls the fluid circuits in response to measured temperatures and pressures as well as certain user defined parameters including the desired cooling profiles.

The illustrated cooling chamber 220 has a plurality of cooling shelves 222 used to cool a large number of vials containing pharmaceutical active ingredients or active biological molecules. A cryogenic cold gas 260 is supplied to the cooling chamber 220 from a static in-line mixer 263 that mixes liquid nitrogen from the source of liquid nitrogen 230 via the liquid supply circuit 232 with a precisely metered gaseous nitrogen gas stream from the gas supply circuit 242 and recirculating cryogenic gas 250 from the gas recirculation circuit 252.

The temperature of the cryogenic cold gas 260 is preferably measured with a temperature sensor 264 disposed downstream of the static in-line mixer 263. By precisely adjusting the flow of nitrogen from the liquid supply circuit 232 with nitrogen gas from the gas supply circuit 242 and the gas recirculation circuit 252 it is possible to rapidly shift the temperature of the cryogenic cold gas 260 which allows cooling of the vials in the cooling chamber 220 with a wide range of cooling profiles to optimize operating conditions and maximize cell viability, biological activity, drug uniformity, as well as drug potency.

Once a cryogenic cold gas 260 is formed by mixing this nitrogen gas with liquid nitrogen, it is split into multiple levels of cooling shelves 222 in a single cooling chamber 220. To provide the exact split of the cryogenic cold gas 260 to the multiple cooling shelves 222, a plurality of critical flow orifices 265 are used to split cryogenic cold gas 260 into multiple gas streams. Under critical choke flow conditions, the cryogenic cold gas flow to the cooling shelves 222 is maintained independent of the downstream pressure. A large cryogenic cold gas manifold 266 is used to eliminate or minimize pressure differences upstream of the critical flow orifices 265 while the downstream gas flow resistance has no impact on the gas flow through the critical flow orifices 265. In this manner, the cryogenic cold gas flow to each of cooling shelves 222 in the cooling chamber 220 is nearly identical.

The cryogenic chiller system 210 is a direct contact cooling system with a cryogenic cold gas 260 flowing in the same direction with respect to each vial and preferably along the longitudinal axis of the vials, thus creating a uniform cooling profile for all the vials. A porous metallic membrane (See FIGS. 1 and 2) provides uniform resistance across all the cooling surfaces, thus allowing the individual vials to receive identical or uniform amounts of refrigeration.

The nitrogen gas supply 240 is preferably received from a bulk storage tank and is directed through a filter 244 to remove particulate materials. The nitrogen gas supply 240 is then regulated down to the desired pressure through a discharge pressure regulator 245. Line pressures before and after the pressure regulator 245 are preferably monitored using one or more pressure indicators 246. A mass flow controller 247 including a mass flow sensor 248 with electro-pneumatic control valve 249 is preferably used to control and maintain a precisely metered nitrogen gas flow rate through the gas supply circuit 242 to the static in-line mixer 263. An electrical solenoid valve 243 is also included in the gas supply circuit 242 to provide positive shut off capability when the cryogenic chiller system 210 is not operating. Alarms can be set in the control system 270 to deactivate this solenoid valve 243 if emergency shut down of the cryogenic chiller system 210 is required.

The illustrated system depicts an additional source of gas, namely air, to be used to operate various control valves. The illustrated air supply circuit 215 includes a filter 216 adapted to remove any particulates from the line, a pressure regulator 218 that is adapted to reduce the air pressure to about 25 psig for safe operation, and one or more pressure indicators 219 used to monitor the pressure in the air supply circuit 215.

The liquid nitrogen supply circuit 232 includes a source of liquid nitrogen 230, a phase separator 234, one or more temperature and pressure sensors 233, a liquid nitrogen manifold 235, one or more safety/relief valves 236, a strainer 237, and a primary cryogenic flow control valve 238. All liquid nitrogen piping is preferably insulated so as to minimize any phase change of the liquid nitrogen to nitrogen gas and the resulting two-phase flow in any of the pipes within the liquid nitrogen supply circuit 232.

The liquid nitrogen phase separator 234 is designed to remove any nitrogen gas that forms in the liquid nitrogen supply circuit 232 due to heat leakage or changes in pipeline pressures. The illustrated phase separator 234 is a double-walled, vertically mounted, cylindrical tank. The inner liquid vessel has a maximum allowable working pressure (MAWP) rating of 250 psig, with the outer vessel providing a vacuum insulation. The gas phase vent valve 239 operatively controls the filling of the phase separator 234 with liquid nitrogen from the source of liquid nitrogen 230. At a low liquid level, the gas phase vent valve 239 opens to vent 280 vapor pressure from the phase separator 234, allowing liquid nitrogen to transfer from the source of liquid nitrogen 230. As the liquid nitrogen level increases in the phase separator 234, gas phase vent valve 239 begins to close and the fill rate decreases until the valve 239 is completely closed and filling of the phase separator 234 with liquid nitrogen stops.

The strainer 237 is coupled to a blow-down relief valve 236A that is operated as required to clean the strainer 237 or purge any vaporized nitrogen gases from the liquid nitrogen supply circuit 232. The strainer 237 also serves to filter out any particulates in the liquid nitrogen so as to avoid adverse performance or damage to the primary cryogenic control valve or relief valves.

One of the illustrated safety valves is a cryogenic electrical solenoid valve 236B that provides positive shutoff of the liquid nitrogen supply. Deactivating the electrical solenoid valve 236B shuts off all liquid nitrogen flow through the liquid nitrogen supply circuit and to the static in-line mixer 263. This electrical solenoid valve 236B is configured such that cutting electrical power immediately stops the liquid nitrogen flow through the liquid nitrogen supply circuit 232 circuit and vent 280 any trapped liquid nitrogen from the circuit. In addition, other process shutdown and the emergency shutoff procedures within the control system 270 generate command signals to the one or more safety valves 236 as, for example, when the cryogenic chiller system 210 has stopped operating at the end of the freezing cycle or for other reasons including preset alarm conditions. The control system 270 stops the liquid nitrogen flow in the liquid nitrogen supply circuit 232 by shutting off one or more of the safety valves 236.

The primary cryogenic flow control valve 238 receive signals from the control system 270 to control the amount of liquid nitrogen supplied to the cryogenic cold gas circuit 262 in response to measured temperatures and pressures within the cryogenic chilling system 210 as well as certain user defined parameters including the desired cooling profiles.

Liquid nitrogen from the liquid nitrogen supply circuit 232 is directed to the static in-line mixer 263. The liquid nitrogen evaporates into a cryogenic cold gas 260 by mixing with the nitrogen gas directed from the gas supply circuit 242 and the gas recirculation circuit 252. The static in-line mixer 263 is used to ensure that no slug of unevaporated liquid nitrogen enters the cooling chamber 220. The temperature in the cryogenic cold gas circuit 262 is monitored with a temperature sensor 264 disposed at or near the exit of the static in-line mixer 263. The control system 270 receives this measured temperature and regulates the liquid nitrogen flow rate and gas flow rates to the static in-line mixer 263 in response thereto based on programmed temperature profiles and preset parameters to adjust the temperature of the cryogenic cold gas.

Downstream of the static in-line mixer 263, the cryogenic cold gas 260 is directed to a large cryogenic cold gas manifold 266 and then to the multiple cooling shelves 222 in the cooling chamber 220 via a plurality of critical flow orifices 265. The large cryogenic cold gas manifold 266 is used to ensure that all the gas distribution points realize the same or similar pressures. The actual cryogenic cold gas flow rate delivered to each of the cooling shelves 222 of the cooling chamber 220 is determined by the size of the critical flow orifice 265 associated with each cooling shelf 222.

Inside the cooling chamber 220 at each level, there are a series of gas distribution pipes with downward oriented nozzles. The purpose of the additional gas distribution pipes inside the cooling chamber is to avoid or minimize velocity generated local pressure gradients that may impact the cryogenic cold gas distribution across any large porous metallic membrane. With the critical flow orifices 265 and gas distribution networks, a large cooling chamber can be used holding thousands of vials or packages with very high degree of cooling uniformity.

The cooling surfaces within the multiple levels of the cooling chamber 220 are made of porous metallic membranes 227 adapted to generate uniform gas flow across the plurality of vials. Due to the small pore size and high flux in the metallic membranes 227, a laminar flow rising from the entire cooling surface is generated. While a laminar flow from the cooling surface is preferred, a turbulent gas flow is tolerable so long as the flow remains parallel to the vials and that macro recirculation of the gas does not occur inside the cooling chamber 220.

Above the porous metallic membranes at each level in the cooling chamber 220 is an exhaust manifold 225 with a perforated plate disposed in a parallel orientation with the porous metallic membranes 227 to maintain the uniform flow of the cryogenic cold gas 260 during the cooling of the vials. The gas received in the exhaust manifold 225 is immediately removed from the cooling chamber 220 in order to avoid or minimize any internally recirculating flow of the spent nitrogen gas. It is important to avoid the internal recirculation of the nitrogen gas as such recirculated gas is generally at a warmer temperature than the cryogenic cold gas 260 supplied to the cooling chamber 220. Such internally recirculating flow is the main cause of temperature non-uniformity with edge effects in prior art or conventional laminar cooling devices.

The exhausted gas removed from the cooling chamber 220 is preferably diverted to a gas recirculation circuit 252. The illustrated gas recirculation circuit 252 includes a recirculating gas manifold 253 disposed between the exhaust manifolds 225 in the cooling chamber 220 and a recirculating blower 254 that starts automatically during the later part of the freezing cycle. The gas recirculation circuit 252 also includes a mass flow meter 255 coupled to the control system 270 that measures the flow through the gas recirculation circuit 252 so as to adjust the make up gas flow rate from the gas supply circuit 242 to maintain a desired level of cryogenic cold gas 260 flow in the cryogenic cold gas circuit 262. Back pressure regulator 256 maintains the pressure from the recirculating blower 254 while check valve 258 keeps the make up nitrogen gas from the gas supply circuit 242 from entering the gas recirculation circuit 252 when the recirculation blower 254 is not operating. Safety relief valve 259 provides overpressurization protection for cooling chamber 220 in case there are blockages in gas recirculation circuit 252.

The pressure and temperature inside the cooling chamber 220 are monitored with pressure gauge 228 and temperature sensors 229 or thermocouples disposed within the cooling chamber 220 proximate some of the vials. The pressure gauges 228, temperature sensors 229 as well as the thermocouples are coupled to and provide inputs to the control system 270.

The above disclosed cryogenic chiller system is able to provide uniform temperatures and flows of cryogenic cold gas to each vial due to the disclosed uniform laminar flow, or turbulent flow with limited macro recirculation, of cryogenic cold gas parallel to the longitudinal axis of the vials or containers. In some embodiments, this flow may be approximated as a plug flow through cooling chamber 220 delivering a uniform temperature and flow rate of cryogenic cold gas to each of the vials of material.

Figure 10:
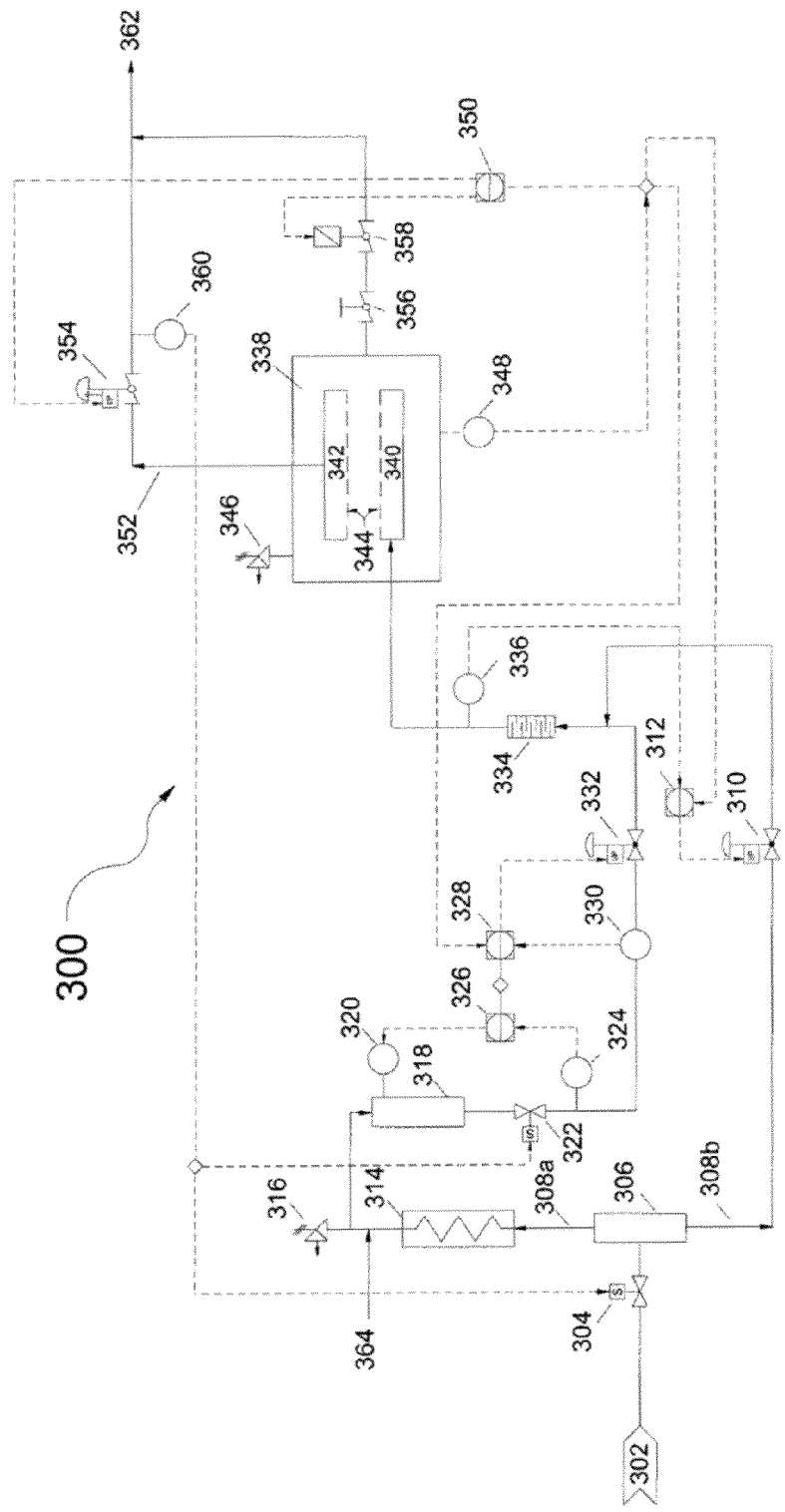
FIG. 10 depicts another embodiment of a multi-batch or commercial scale uniform flow cooling system with more detailed views of the process and instrumentation.

FIG. 10 presents another embodiment of a cryogenic chiller system 300. In this particular embodiment, a source of liquid cryogen 302 acts as the supply source for both the liquid cryogen and gas flows in the cryogenic chiller system. The liquid cryogen source may include, but is not limited to liquid: argon, nitrogen, air, permissible mixtures thereof, and any other appropriate cryogen that is non-reactive with the system and material to be cryopreserved. The source of liquid cryogen 302 is connected to a safety valve 304. In one embodiment safety valve 304 is an electronically controlled solenoid valve. Safety valve 304 shuts off the flow of cryogen to the system when the system is de-energized, the pressure in the exhaust system is greater than or equal to the pressure in the cooling chamber, a manual safety switch has been thrown, a preset alarm activates, or other appropriate situations. When safety valve 304 is open liquid cryogen is supplied to phase separator 306. Phase separator 306 has two output flows to conduits 308a and 308b.

The first flow provided from phase separator 306 flows through conduit 308a. This first flow provides liquid cryogen or a mix of liquid cryogen and gas to vaporizer 314. Vaporizer 314 vaporizes any liquid cryogen present in the flow to create a flow of gas. The vaporizer is connected to a pressure relief valve 316 and heater 318. In a preferred embodiment, pressure relief valve 316 is set to 100 psi (gauge). Heater 318 heats the gas flow to adjust the temperature to that indicated by the control systems. Temperature sensor 324 monitors the temperature of the gas flow exiting heater 318 and outputs a signal to temperature controller 326. Temperature controller 326 actuates a relay 320 to control heater 318. In a preferred embodiment relay 320 is a solid state relay. However, relay 320 may be replaced with a circuit or other suitable component capable of receiving instructions from temperature controller 326 and controlling heater 318. The flow of temperature adjusted gas is provided from heater 318 through safety valve 322 to flow control valve 332. A flow sensor 330 monitors the flow of temperature adjusted gas and outputs a signal to flow controller 328. Flow controller 328 controls flow control valve 332 which in turn controls the flow rate of temperature adjusted gas provided to mixer 334.

The second flow provided from phase separator 306 is liquid cryogen flowing through conduit 308b. The flow of liquid cryogen is directed through flow control valve 310. Flow control valve 310 controls the flow rate of liquid cryogen. The flow of liquid cryogen is combined with the flow of temperature adjusted gas provided to mixer 334. All conduits, valves, and control systems associated with transporting the liquid cryogen are preferably insulated to minimize any unwanted phase change of the liquid cryogen to a gas.

The separate flows of temperature adjusted gas from flow control valve 332 and liquid cryogen from flow control valve 310 are mixed together in mixer 334 to provide cryogenic cold gas. In some embodiments, mixer 334 may be a static mixer, an arrangement of valves, an impeller, or any other appropriate structure adapted for mixing the flows. The temperature of the cryogenic cold gas is monitored by temperature sensor 336 after exiting mixer 334. Temperature sensor 336 provides a signal to temperature controller 312. Temperature controller 312 adjusts the flow of cryogen through flow control valve 310 so as to adjust the temperature of the cryogenic cold gas exiting mixer 334.

The flow of cryogenic cold gas is provided to cooling chamber 338 holding a plurality of vials or containers. The cryogenic cold gas flows through the chamber so as to transfer heat with the vials or containers. To provide uniform cooling of each vial or container, the cryogenic cold gas is uniformly distributed throughout cooling chamber 338 by at least one gas injection box 340. The cryogenic cold gas is immediately exhausted from the cooling chamber by at least one gas exhaust box 342 preferably arranged above the at least one gas injection box 340. The cryogenic cold gas is immediately exhausted to avoid any recirculation of the cryogenic cold gas since this will lead to non-uniformities in the cooling chamber's 338 temperature. Cooling chamber 338 is further provided with pressure relief valve 346 preferably set at 50 psig. Pressure sensor 348 monitors the pressure in cooling chamber 338. A signal is output from pressure sensor 348 to liquid nitrogen controller 312, gas flow controller 328, and pressure controller 350. Pressure controller 350 controls flow control valves 354 and 358. In some embodiments, the system may reduce or shut down the liquid and gas flows during pressurization and depressurization steps in response to a signal from pressure sensor 348.

In a preferred embodiment, porous membranes 344 suitable for cryogenic use are attached to the gas injection box 340 and gas exhaust box 342. The porous membranes 344 are adapted to generate a uniform flow of gas across the plurality of vials. Due to the small pore size and high flux across the porous membranes 344, a laminar flow rising from the entire cooling surface is generated. In a preferred embodiment, porous membranes 344 are porous metallic plates. While a laminar flow from the cooling surface is preferred, a turbulent gas flow is tolerable so long as the flow remains parallel to the vials and that macro recirculation of the gas does not occur inside the cooling chamber 338. While the flow is disclosed as flowing upwards it should be understood that the flow of gas may be oriented in any direction so long as each of the vials receives a uniform flow and temperature of cryogenic cold gas.

The cryogenic cold gas exhausted through the at least one exhaust hood 342 flows through conduit 352 to adjustable pressure control valve 354 prior to being exhausted to system exhaust 362. Adjustable pressure control valve 354 enables pressurization of cooling chamber 338. The pressure of the exhausted cryogenic cold gas is monitored by pressure switch 360. Pressure switch 360 actuates safety valves 304 and 322 when the pressure of the exhausted cryogenic cold gas is greater than the pressure in cooling chamber 338. Closing safety valves 304 and 322 stops the flows of liquid and gas into the system thus preventing nitrogen leakage due to abnormal system operation.

Cooling chamber 338 further includes an adjustable flow control valve 356 connected to flow control valve 358. Adjustable flow control valve 356 may be adapted for either manual or electronic adjustment. In one possible embodiment, flow control valve 358 is an on/off control valve actuated by a pneumatic solenoid. In other alternative embodiments, flow control valve 358 may be actuated by an electrical solenoid, an electrical switch, a pneumatic control system, a hydraulic control system, or any other appropriate mechanism. When open, flow control valve 358 enables the depressurization of cooling chamber 338 to system exhaust 362. The rate of depressurization is controlled by the setting of adjustable flow control valve 356.

In a preferred embodiment, at least a portion of the cryogenic cold gas exhausted through system exhaust 362 is recycled into the system. The recycled gas is preferably input into the gas flow between vaporizer 314 and heater 318 depicted as recycled exhaust gas input 364. However, it is possible to place the recycled exhaust gas input 364 in other alternative positions within the system.

It should be understood that the separate valves and systems depicted herein may be powered and controlled in a variety of ways. Possible methods of providing power and control include, but are not limited to, manual, electrical, pneumatic, and hydraulic control. In addition, cryogenic chiller system 300 may implement any combination of the above methods to provide power and control to the separate components. The selection and application of these different control and power methods merely represents a design choice and can be easily implemented by one of skill in the art.

While the above described methods and systems have been shown with regards to providing uniform temperature profiles during a freezing process, the same methods and systems may be applied to provide a uniform temperature profile for a plurality of vials or containers for uniformly thawing the material in each of the plurality of vials or containers. In both a uniform freezing and thawing process, each vial or container sees substantially the same temperature profile regardless of its location within the cooling chamber. Similar to providing a uniform temperature profile during freezing, uniform thawing of a plurality of vials or containers will result in more repeatable uniform properties. Such properties include, but are not limited to, cell viability, functionality, and/or biological activity. Depending upon the type of biological material present in each container or vial, the biological material is revived during the thawing process. Reviving the biological material entails returning the biological material to its original state prior to the freezing process. Furthermore, while such systems are typically used for one type of material at a time it is possible to freeze multiple biological materials at once inside the system. Therefore, it is possible that at least two of the containers inside of the system would contain different biological materials during a freezing process. Such a use is considered within the scope of this disclosure.

The above disclosed systems and methods are particularly well-suited for commercial type or large scale biological production operations since the process is conducted using the same equipment and process parameters that are easily scaled or adapted to manufacture a wide range of biological products. The presently disclosed process and system provides for the controlled rate freezing of biological materials using a process that achieves a high degree of uniformity in cooling or freezing of the biological material from sample to sample, vial to vial, container to container, and batch to batch.

Nucleation Control

In addition to the temperature profile seen by each vial or container, the final uniformity of properties and structure from sample to sample, vial to vial, container to container, and batch to batch may also depend on the nucleation temperature. As stated above, this variability in the nucleation temperature can impact properties such as cell activity and viability as well as the crystal structure of the frozen material and the time needed to complete a freeze drying process. Advantageously, the currently disclosed systems and processes may be applied to provide control over the nucleation temperature of the material in the plurality of vials or containers using two possible methods. The methods include, but are not limited to, pressure control induced nucleation and temperature quench induced nucleation, although nucleation control need not be used in all embodiments. The above disclosed processes and systems may also be modified to apply any other appropriate nucleation method including, but not limited to, additives, ice fog, vial pretreatment, vibration, and vacuum freezing.

Nucleation is the onset of a phase transition in a small region of a material. For example, the phase transition can be the formation of a crystal from a liquid. The crystallization process (i.e., formation of solid crystals from a solution) often associated with freezing of a solution starts with a nucleation event followed by crystal growth.

In the crystallization process, nucleation is the step where selected atoms and/or molecules dispersed in the solution or other material start to gather to create clusters in the nanometer scale so as to become stable under the current operating conditions. These stable clusters constitute the nuclei. The clusters need to reach a critical size in order to become stable nuclei. Such critical size is usually dictated by the operating conditions such as temperature, contaminants, degree of supersaturation, etc. and can vary from one sample of the solution to another. It is during the nucleation event that the atoms in the solution arrange in a defined and periodic manner that defines the crystal structure.

Crystal growth is the subsequent growth of the nuclei that succeed in achieving the critical cluster size. Depending upon the conditions either nucleation or crystal growth may predominate over the other, and as a result, crystals with different sizes and shapes are obtained. Control of crystal size and shape constitutes one of the main challenges in industrial manufacturing, such as for pharmaceuticals.

In addition to temperature control, the present methods and systems may be used for controlling the time and/or temperature at which a nucleated phase transition occurs in a material. In freezing applications, the probability that a material will spontaneously nucleate and begin changing phase is related to the degree of sub-cooling of the material and the absence or presence of contaminants, additives, structures, or disturbances that provide a site or surface for nucleation.

The freezing or solidification step is particularly important in cryopreservation and freeze-drying processes where existing techniques result in nucleation temperature differences across a multitude of vials or containers. The nucleation temperature differences tend to produce a non-uniform product and an excessively long drying time for freeze-drying processes. The present methods, on the other hand, provide a higher degree of process control in batch solidification processes (e.g., freeze-drying) and produce a product with more uniform structure and properties. Unlike some of the prior art techniques to induce nucleation, the present methods require minimal equipment and operational changes for implementation.

In principle, the present methods can be applied to any material processing step that involves a nucleated phase transition. Examples of such processes include the freezing of a liquid, crystallization of ice from an aqueous solution, crystallization of polymers and metals from melts, crystallization of inorganic materials from supersaturated solutions, crystallization of proteins, artificial snow production, deposition of ice from vapor, food freezing, freeze concentration, fractional crystallization, cryopreservation, or condensation of vapors to liquids. From a conceptual standpoint, the present methods may also be applied to phase transitions such as melting and boiling.

The presently disclosed methods represent an improvement to current pharmaceutical cryopreservation and lyophilization processes. For example, within a large industrial system there can be over 100,000 vials containing a pharmaceutical product that needs to be frozen and/or dried. Current practice in the industry is to cool the solution to a very high degree so that the solution in all vials or containers in the freeze-dryer are guaranteed to freeze. However, as discussed above, the non-uniform cooling and lack of a uniform and consistent nucleation control method, the contents of each vial or container freezes randomly over a range of temperatures below the freezing point.

Figure 6:
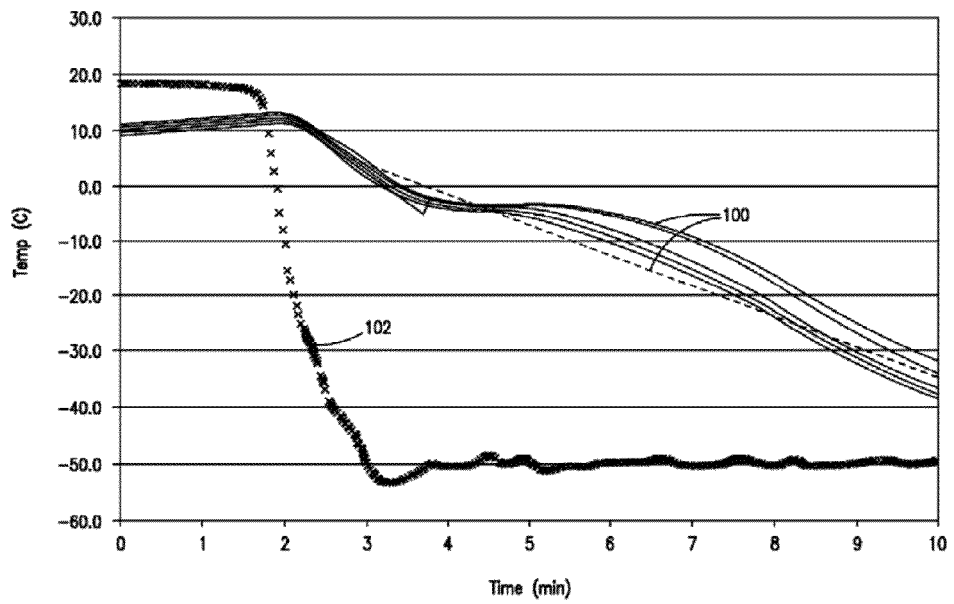
FIGS. 6 through 8 depict selected temperature profiles of the cryogenic cold gas and corresponding relationship to the cooling rates of biological materials contained in multiple vials.
Figure 7:
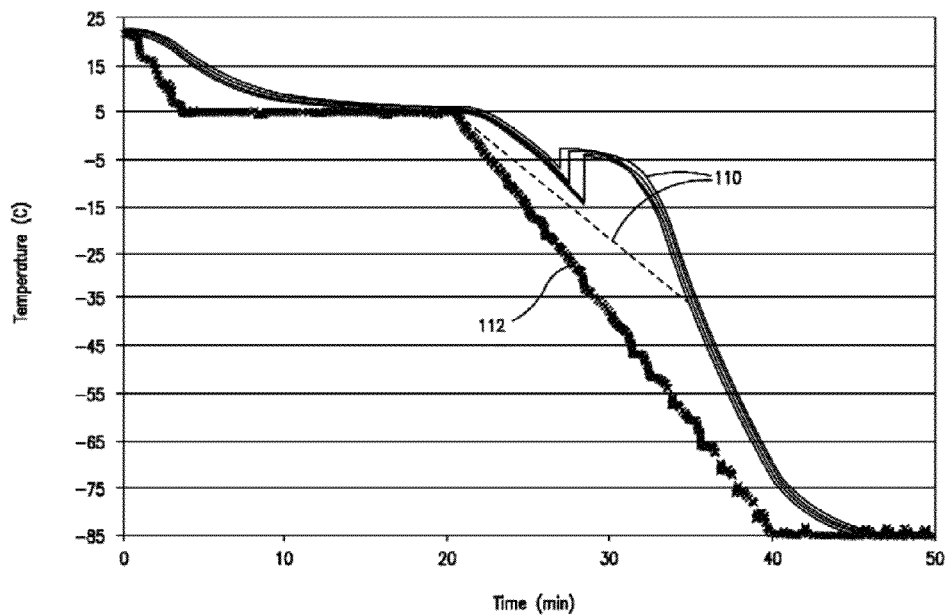
Figure 8:
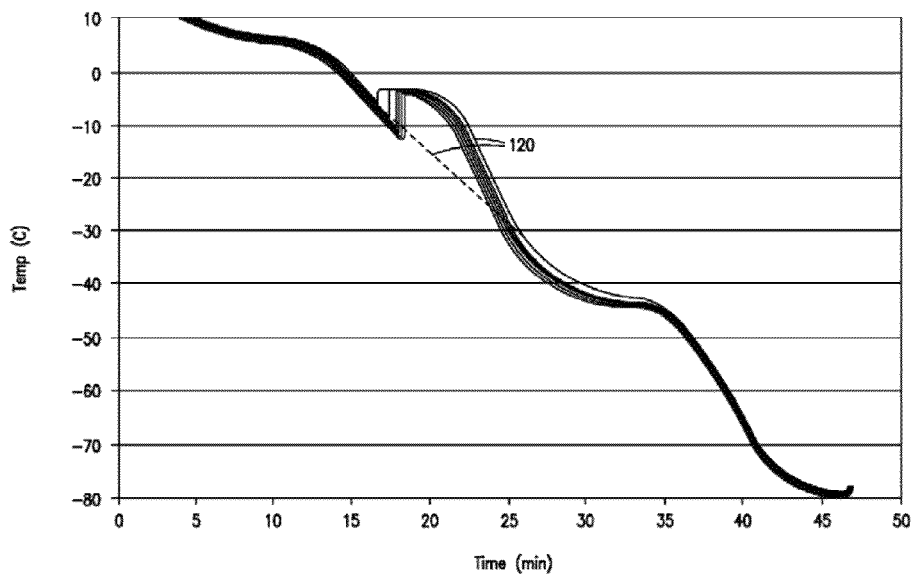

Turning now to a closer examination of FIGS. 6-8, the plotted temperature profiles illustrate that the presently disclosed freezing or chilling process and system can be used to initiate and control the nucleation of freezing in materials using a temperature quench. As illustrated in FIGS. 6-8, the onset of nucleation of freezing of the materials in all vials monitored occurred at roughly the same time and same temperature. Nucleation of freezing is exhibited by the concurrent short spike in sample temperature (see 100, 110, 120) as a result of the exothermic process occurring during the phase change occurring in the samples. Thus, nucleation control is possible by precisely controlling the timing and magnitude of a sharp or rapid temperature quench using the above described controlled freezing systems and methods. Alternatively, a temperature quench may be referred to as a temperature spike or cold spike in reference to the same physical process described above. In certain embodiments the change in temperature during the temperature quench may be a stepwise change in temperature or it may change at a predetermined rate.

In a broad sense, the presently disclosed methods for inducing the onset of nucleation of a phase transition within a material via temperature quench nucleation control comprise the steps of: (i) uniformly cooling the material to a temperature near or below a phase transition temperature of the material; and (ii) uniformly and rapidly decreasing the temperature of the cryogenic cold gas to induce nucleation of the material. Each of these important steps will be discussed in more detail below.

Figure 11:
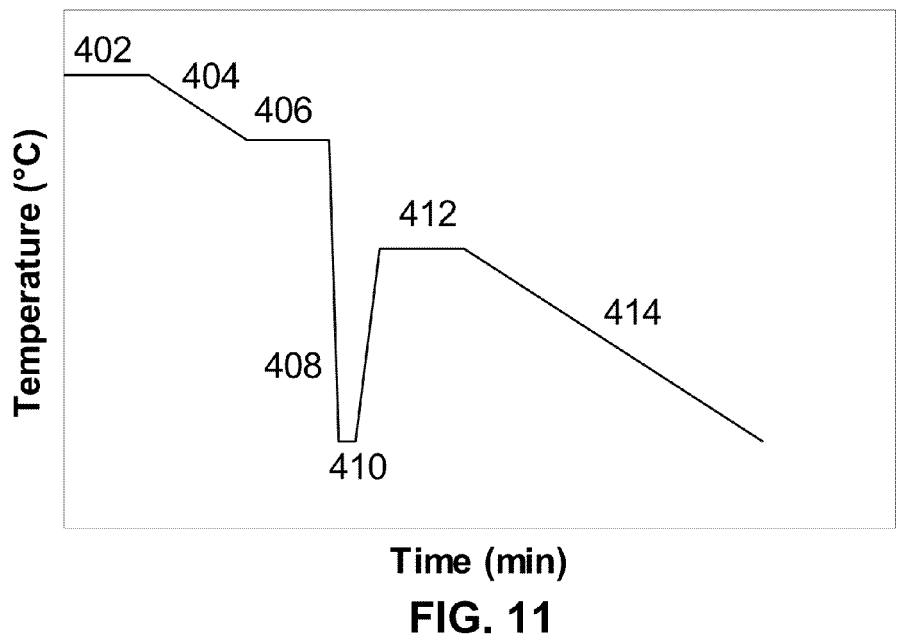
FIG. 11 is an illustrative temperature profile of the cryogenic cold gas during a temperature quench induced nucleation freezing process.

FIG. 11 presents a more detailed exemplary temperature profile of the cryogenic gas during a freezing process using a temperature quench to control nucleation. The temperature profile versus time comprises an equilibrium step 402, a cooling step 404, a pre-nucleation temperature step 406, a temperature quench step 408, a temperature quench hold step 410, a post-nucleation temperature hold step 412, and a final cooling step 414.

During equilibrium step 402 each of the vials or containers in the system are brought to a uniform equilibrium temperature near or below the freezing point (i.e. the phase transition temperature) of the material prior to beginning the remaining steps in the freezing process. After each vial or container reaches a uniform temperature, the vials or containers are further cooled by decreasing the cryogenic cold gas to a pre-nucleation temperature during steps 404 and 406. The change in temperature of the cryogenic cold gas may decrease linearly as indicated in step 404 and then hold steady as shown in step 406, or alternatively the temperature of the cryogenic cold gas may stepwise change to the pre-nucleation temperature indicated in step 406 without the need for the linear, or optionally non-linear, temperature change shown in step 404. Furthermore, the cryogenic cold gas may be held at the pre-nucleation temperature for a predetermined time as indicated in step 406 to ensure all vials or containers reach a uniform temperature prior to nucleating the phase change. Optionally, steps 404 and 406 may be performed dynamically without the hold time shown in step 406.

The material is nucleated in temperature quench step 408. During step 408, the temperature of the cryogenic cold gas is adjusted to a temperature sufficiently low to ensure nucleation of the material in each vial or container. In a preferred embodiment, the temperature adjustment of the cryogenic cold gas is sufficiently fast such that the temperature of the material in each of the vials or containers does not substantially change during the temperature adjustment. After nucleating the material in each vial or container an optional temperature quench hold may be applied at step 410.

After performing temperature quench hold step 410 the temperature of the cryogenic cold gas is subsequently raised to a temperature below the freezing point of the material and held for a set amount of time during the post-nucleation temperature hold step 412 to ensure uniform temperature. After step 412, the cryogenic cold gas is cooled at a predetermined rate to a final desired temperature during final cooling step 414.

Figure 12:
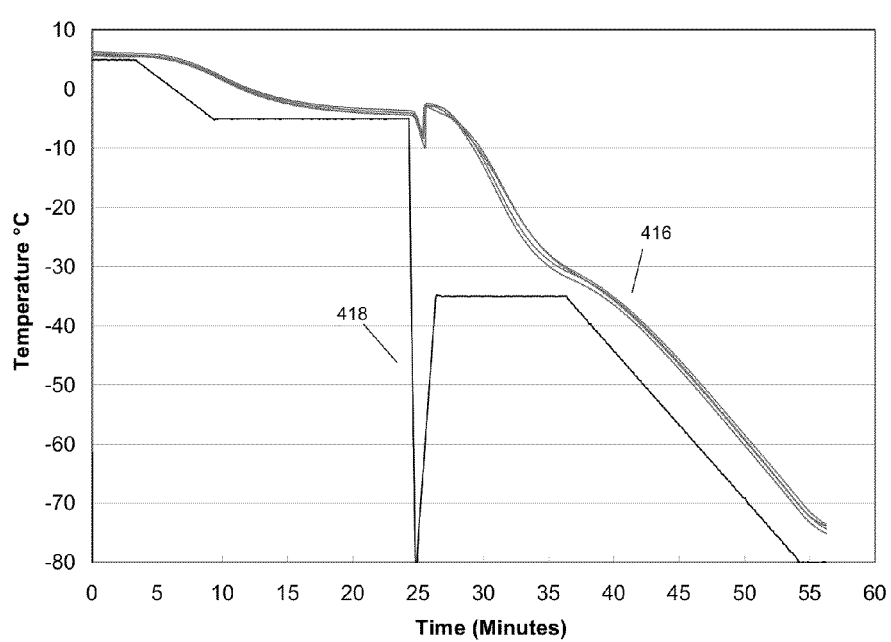
FIG. 12 is a graph depicting the temperature profiles of different samples during a temperature quench induced nucleation freezing process.
Figure 13:
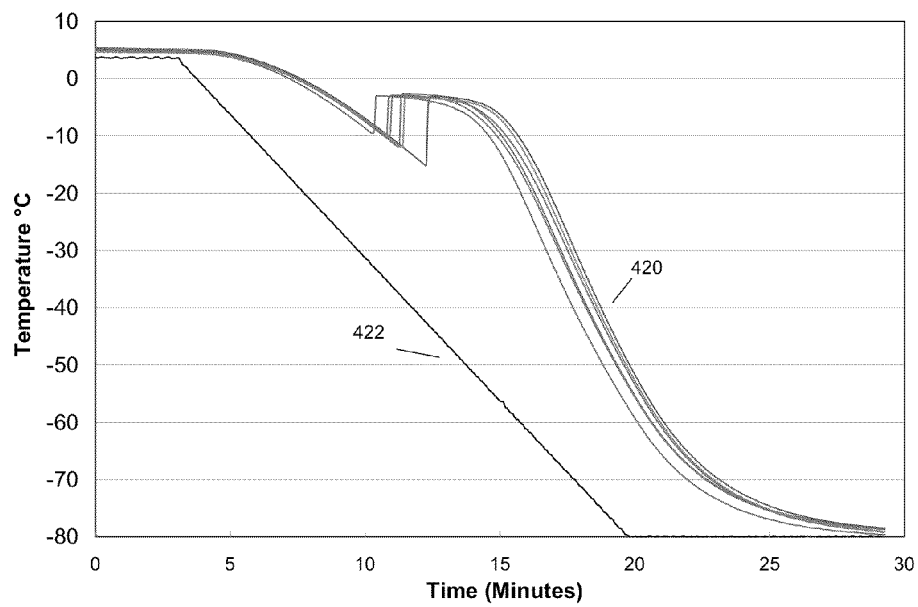
FIG. 13 is a graph depicting the temperature profiles of different samples during a freezing process with no nucleation control.

FIG. 12 depicts the temperature profiles 416 of six separate vials and the cryogenic cold gas temperature profile 418 during a freezing process implementing temperature quench induced nucleation control. The cryogenic cold gas profile 418 included a pre-nucleation temperature of −5° C., a quench temperature of −80° C., a post nucleation temperature of −35° C., a post-nucleation hold time of 10 minutes, and a post-nucleation cooling rate of 2.5° C./min. In contrast FIG. 13 depicts the temperature profiles 420 of six separate vials and the cryogenic cold gas temperature profile 422 during a freezing process without nucleation control. The cryogenic cold gas profile 422 had a cooling rate of 5° C./min. As indicated by the sharp increase in temperature along each temperature profile, the samples that underwent the freezing process with nucleation control exhibit nucleation temperatures and times in a narrower range than those in the freezing process without nucleation control. Consequently, the freezing process with nucleation control enables more uniform and repeatable sample temperature profiles.

When compared to the wide spectrum of times and temperatures in the nucleation of freezing that results from use of conventional controlled rate freezers, the present system and method applying nucleation control via a temperature quench provides a greater degree of control which likely impacts other performance aspects and characteristics of the preserved biological material. Also, as the contemplated nucleation initiation and control is temperature driven, it works equally well in open or closed containers or vials.

Figure 14:
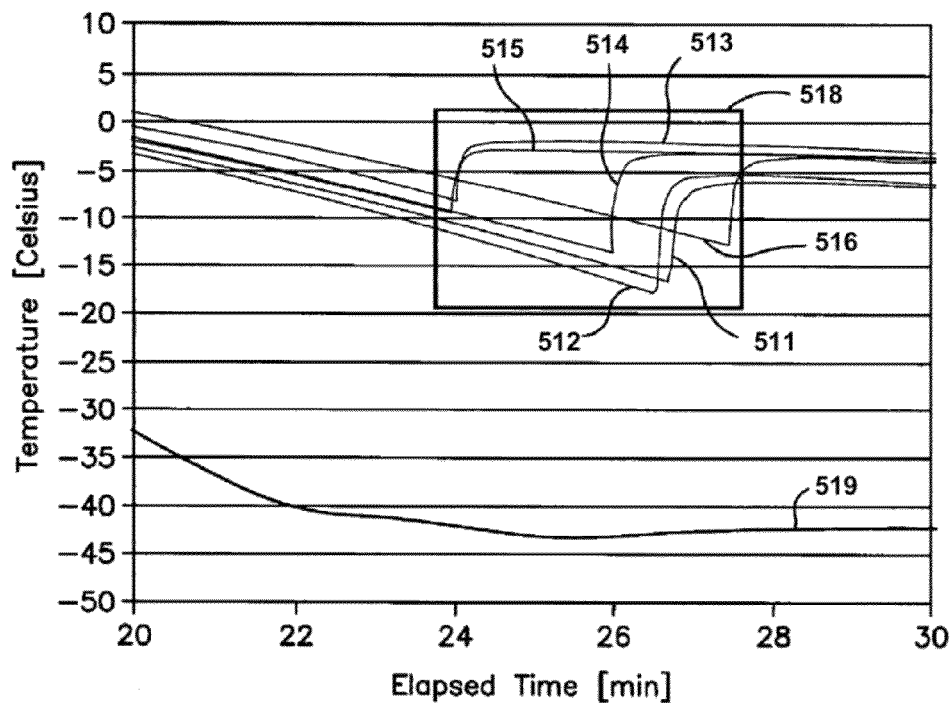
FIG. 14 is a graph depicting the temperature versus time plot of a solution undergoing a stochastic nucleation process and further showing the range of nucleation temperatures of the solution.

As shown above in FIG. 10, pressure control systems may be included to permit pressurization and depressurization control of the system and freezing process in addition to uniform temperature control. Therefore, in addition to controlling the nucleation temperature via a temperature quench method, the nucleation temperature may be controlled using pressure induced nucleation. FIG. 14 depicts a temperature versus time plot of six vials of an aqueous solution undergoing a conventional stochastic nucleation process while in a conventional freeze dryer using a cold shelf arrangement. The plot shows a typical range of nucleation temperatures of the solution within the vials (511,512,513,514,515, and 516). As seen therein, the vial contents have a thermodynamic freezing temperature of about 0° C., yet the solution within each vial naturally nucleates over the broad temperature range of about −7° C. to −20° C. or more, as highlighted by area 518. Plot 519 represents shelf temperature inside the freeze-drying chamber.

Figure 15:
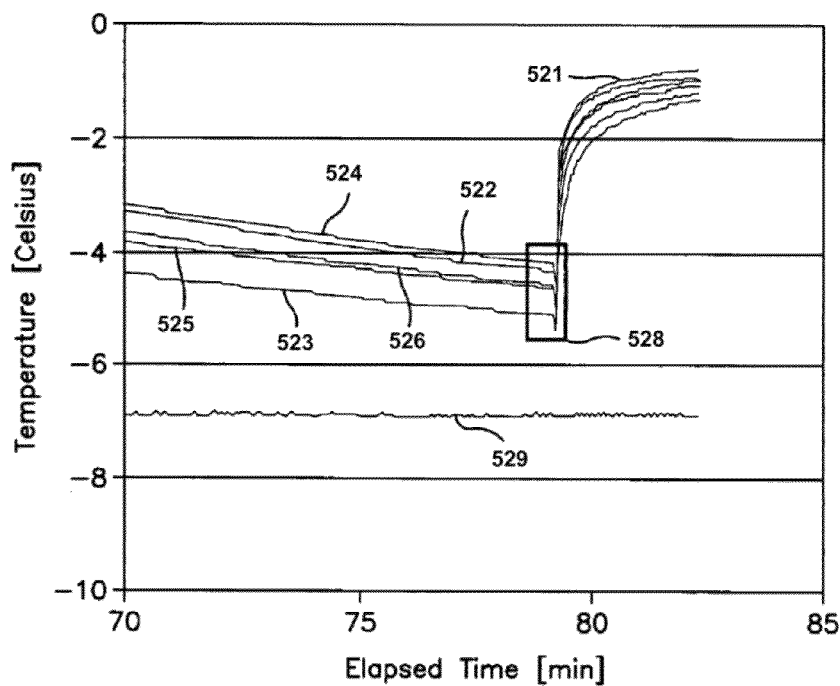
FIG. 15 is a graph depicting the temperature versus time plot of a solution undergoing an equilibrated cooling process with depressurized nucleation.
Figure 16:
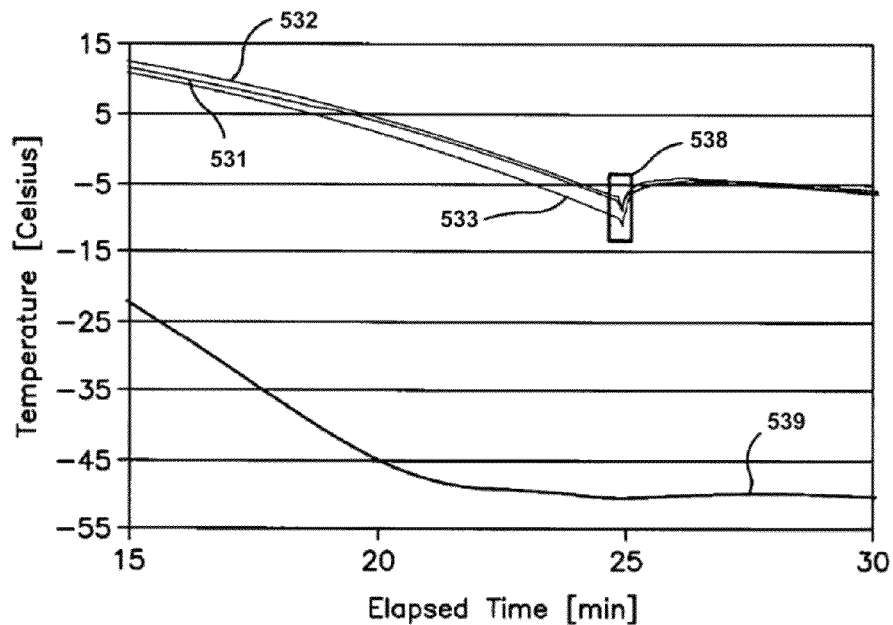
FIG. 16 is a graph depicting the temperature versus time plot of a solution undergoing a dynamic cooling process with depressurized nucleation.

Conversely, FIG. 15 and FIG. 16 depict temperature versus time plots of a solution undergoing a freezing process with depressurized nucleation in accordance with the present methods. In particular, FIG. 15 shows the temperature versus time plot of six vials of an aqueous solution undergoing an equilibrated cooling process (See Example 2) with nucleation induced via depressurization of the chamber (521,522,523, 524,525, and 526). The vial contents have a thermodynamic freezing temperature of about 0° C. yet the solution within each vial nucleates at the same time upon depressurization and within a very narrow temperature range (i.e., −4° C. to −5° C.) as seen in area 528. Plot 529 represents the shelf temperature inside the freeze-drying chamber and depicts an equilibrated freezing process, one where the temperature of the shelves is held more or less steady prior to depressurization.

Similarly, FIG. 16 shows the temperature versus time plot of three vials of an aqueous solution undergoing a dynamic cooling process (See Example 7) with nucleation induced via depressurization of the chamber (531, 532, and 533). Again, the vial contents have a thermodynamic freezing temperature of about 0° C. yet the solution within each vial nucleates at the same time upon depressurization at a temperature range of about −7° C. to −10° C., as seen in area 538. Plot 539 represents the shelf temperature inside the freeze-drying chamber and generally depicts a dynamic cooling process, one where the temperature of the shelves is actively lowered during or prior to depressurization.

As illustrated in FIGS. 14-16, the present pressure induced nucleation method provides improved control of the nucleation process by enabling the freezing of solutions to occur within a more narrow temperature range (e.g., about 0° C. to −10° C.) and/or concurrently, thereby yielding a product with greater uniformity from vial-to-vial. While not demonstrated, it is foreseeable that the induced nucleation temperature range may even extend slightly above the phase transition temperature and may also extend to about 40° C. of sub-cooling.

In a broad sense, the presently disclosed methods for inducing nucleation of a phase transition within a material via pressure control comprise the steps of: (i) uniformly cooling the material to a temperature near or below a phase transition temperature of the material; and (ii) rapidly decreasing the pressure to induce nucleation of the material. Each of these important steps will be discussed in more detail below.

Step 1—Cooling the Material

Illustrative materials useful in the present method include pure substances, gases, suspensions, gels, liquids, solutions, mixtures, or components within a solution or mixture. Suitable materials for use in the present method may include, for example, pharmaceutical materials, biopharmaceutical materials, foodstuffs, chemical materials, and may include products such as wound-care products, cosmetics, veterinary products and in vivo/in vitro diagnostics related products and the like. When the material is a liquid, it may be desirable to dissolve gases into the liquid. Liquids in a controlled gas environment will generally have gases dissolved in them.

Other illustrative materials useful in the present method include biological or biopharmaceutical material such as tissues, organs and multi-cellular structures. For certain biological and pharmaceutical applications, the material may be a solution or mixture that includes: a live or attenuated viruses; nucleic acids; monoclonal antibodies; polyclonal antibodies; biomolecules; nonpeptide analogues; peptides, including polypeptides, peptide mimetics and modified peptides; proteins, including fusion and modified proteins; RNA, DNA and subclasses thereof; oligonucleotides; viral particles; and similar such materials or components thereof.

Pharmaceutical or biopharmaceutical solutions contained in vials or containers for freeze-drying would be a good example of a material that would benefit from the present method. The solutions are mostly water and are substantially incompressible. Such pharmaceutical or biopharmaceutical solutions are also highly pure and generally free of particulates that may form sites for nucleation. Uniform nucleation temperature is important to creating a consistent and uniform ice crystal structure from vial to vial or container to container. The ice crystal structure developed also greatly affects the time required for drying during a freeze drying process.

As applied to a freeze-drying process, the material is preferably placed in a chamber, such as a freeze-drying chamber. Preferably, the chamber is configured so as to allow control of the temperature, pressure, and gas atmosphere within the chamber. The gas atmosphere may include, but is not limited to: argon, nitrogen, helium, air, water vapor, oxygen, carbon dioxide, carbon monoxide, nitrous oxide, nitric oxide, neon, xenon, krypton, methane, hydrogen, propane, butane, and the like, including permissible mixtures thereof. The preferred gas atmosphere comprises an inert gas, such as argon, at a pressure between about 7 to about 50 psig or more. Temperatures within the freeze-dryer chamber are often dictated by the freeze-drying process and are easily controlled via the use of a heat transfer fluid that cools or warms the shelves within the chamber to drive the temperature of the vials or containers and the material within each vial or container.

In accordance with the present methods, the material is cooled to a temperature near or below its phase transition temperature. In the case of an aqueous based solution undergoing a freeze-drying process, the phase transition temperature is the thermodynamic freezing point of the solution. Where the solution reaches temperatures below the thermodynamic freezing point of the solution, it is said to be sub-cooled. When applied to a freezing process of an aqueous-based solution, the present method is effective when the degree of sub-cooling ranges from near or below the phase transition temperature up to about 40° C. of sub-cooling, and more preferably between about 3° C. of sub-cooling and 10° C. of sub-cooling. In some of the examples described below, the present method of inducing nucleation works desirably even where the solution has only about 1° C. of sub-cooling below its thermodynamic freezing point.

Where the material is at a temperature below its phase transition temperature, it is often referred to as being in a metastable state. A metastable state is an unstable and transient, but relatively long-lived, state of a chemical or biological system. A metastable material temporarily exists in a phase or state that is not its equilibrium phase or state. In the absence of any changes in the material or its environment, a metastable material will eventually transition from its non-equilibrium state to its equilibrium state. Illustrative metastable materials include super-saturated solutions and sub-cooled liquids.

A typical example of a metastable material would be liquid water at atmospheric pressure and a temperature of −10° C. With a normal freezing point of 0° C., liquid water should not thermodynamically exist at this temperature and pressure, but it can exist in the absence of a nucleating event or structure to begin the ice crystallization process. Extremely pure water can be cooled to very low temperatures (−30° C. to −40° C.) at atmospheric pressure and still remain in the liquid state. Such sub-cooled water is in a non-equilibrated thermodynamically metastable state. It only lacks a nucleation event to cause it to begin the phase transition whereby it will return to equilibrium.

As discussed above, the present methods of inducing nucleation of a phase transition within a material or freezing a material can be utilized with various cooling profiles, including, for example, an equilibrated cooling environment or a dynamic cooling environment (See FIGS. 15 and 16).

Step 2—Rapidly Decreasing the Pressure

When the material has reached the desired temperature near or below the phase transition temperature, the chamber is quickly or rapidly depressurized. This depressurization triggers the nucleation and phase transition of the solution within the vials or containers. In the preferred embodiment, chamber depressurization is accomplished by opening or partially opening a large control valve that separates the high pressure chamber from either the ambient environment or a lower pressure chamber or environment. The elevated pressure is quickly lowered by mass flow of gas atmosphere out of the chamber. The depressurization needs to be fairly fast to induce the nucleation. The depressurization should be finished in several seconds or less, preferably 40 seconds or less, more preferably 20 seconds or less, and most preferably 10 seconds or less.

In typical freeze-drying applications, the pressure difference between the initial chamber pressure and the final chamber pressure, after depressurization, should be greater than about 7 psi, although smaller pressure drops may induce nucleation in some situations. Most commercial freeze-dryers can readily accommodate the range of pressure drops needed to control nucleation. Many freeze-dryers are designed with pressure ratings in excess of 25 psig to withstand conventional sterilization procedures employing saturated steam at 121° C. Such equipment ratings provide an ample window to induce nucleation following protocols that depressurize from starting pressures above ambient pressure or the pressure in the surrounding environment. The elevated pressure and subsequent depressurization can be achieved through any known means (e.g., pneumatic, hydraulic, or mechanical). In the preferred embodiments, operating pressures for the present methods should remain below the supercritical pressure of any applied gas, and subjecting the material to extreme low pressures (i.e., about 10 mTorr or less) should be avoided during nucleation of the material.

While not wishing to be bound to any particular mechanism, one possible mechanism to explain the controlled nucleation observed in the practice of the presently disclosed depressurized nucleation method is that gases in solution in the material come out of solution upon depressurization and form bubbles that nucleate the material. An initial elevated pressure increases the concentration of dissolved gas in the solution. The rapid decrease in pressure after cooling reduces the gas solubility, and the subsequent release of gas from the sub-cooled solution triggers nucleation of the phase transition.

Another possible mechanism is that the temperature decrease of the gas proximate the material during depressurization causes a cold spot on the surface of the material that initiates nucleation. Another possible mechanism is that the depressurization causes evaporation of some liquid in the material and the resultant cooling from the endothermic evaporation process may initiate the nucleation. Another possible mechanism is that the depressurized cold gas proximate the material freezes some vapor either in equilibrium with the material prior to depressurization or liberated from the material by evaporation during depressurization; the resultant solid particles re-enter the material and act as seeds or surfaces to initiate nucleation. One or more of these mechanisms may contribute to initiation of nucleation of freezing or solidification to differing extents depending on the nature of the material, its environment and the phase transition being nucleated.

The process may be carried out entirely at a pressure greater than ambient pressure or over a range of pressures spanning ambient pressure. For example, initial chamber pressure can be above ambient pressure and the final chamber pressure, after depressurization, can be above ambient pressure but less than the initial chamber pressure; the initial chamber pressure can be above ambient pressure and the final chamber pressure, after depressurization, can be about ambient pressure or slightly below ambient pressure. In addition, the chamber pressure may be increased, prior to depressurization, while uniformly cooling the samples or the step of increasing the pressure may be carried out in a separate distinct step.

The rate and magnitude of the pressure drop are also believed to be an important aspect of the present methods. Experiments have shown that nucleation will be induced where the pressure drop ($\Delta P$) is greater than about 7 psi. Alternatively, the magnitude of the pressure drop may be expressed as an absolute pressure ratio, $R=P_i/P_f$, where $P_i$ is initial absolute pressure and $P_f$ is final absolute pressure. It is believed that nucleation may be induced upon depressurization where the absolute pressure ratio, R, is greater than about 1.2 in many practical applications of the present methods. The rate of pressure drop also plays an important role in the present methods. One method of characterizing the rate of pressure drop is through use of a parameter, A, where $A=\Delta P/\Delta t$. Again, it is surmised that nucleation will be induced for values of A greater than a prescribed value, such as about 0.2 psi/sec. Empirical data through experimentation should aid one to ascertain the preferred pressure drop and rate of pressure drop.

Figure 17:
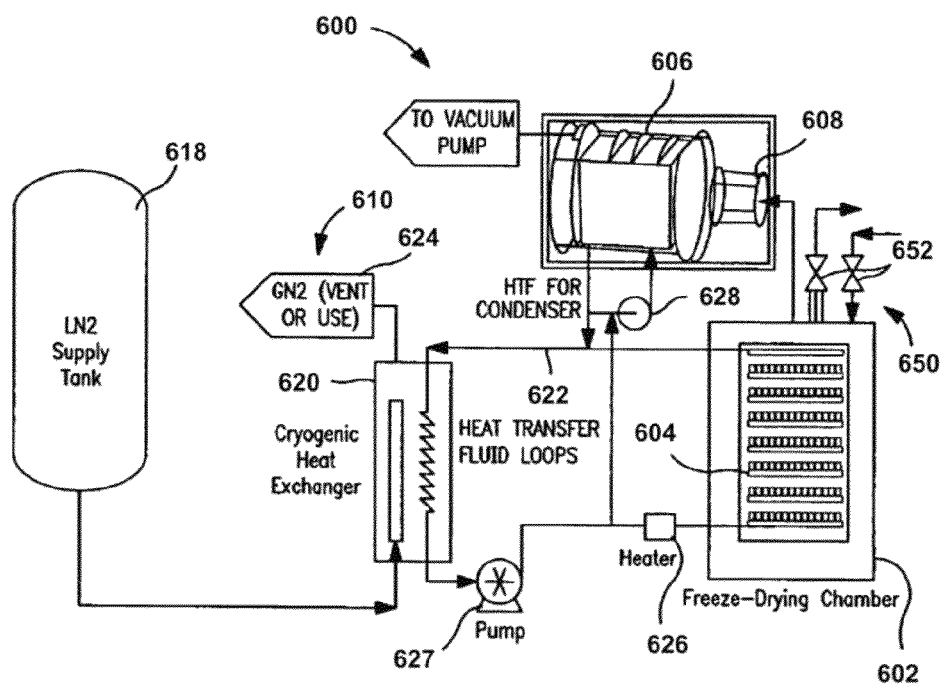
FIG. 17 is a schematic representation of a lyophilization system in accordance with the present invention.

The above disclosed method of inducing nucleation via pressure control may be implemented in a conventional freeze-dryer or the currently disclosed uniform flow cryogenic chiller. Turning now to FIG. 17, a freeze-dryer is illustrated as freeze-dryer unit (600) which has various main components plus additional auxiliary systems to carry out a lyophilization cycle. In particular, the freeze-dryer unit (600) includes a lyophilization chamber 602 that contains the shelves 604 adapted to hold vials or containers of the solution to be lyophilized (not shown). The solution to be lyophilized is specially formulated and typically contains the active ingredient, a solvent system and several stabilization agents or other pharmaceutically acceptable carriers or additives. Lyophilization of this formulation takes place from specialized containers located on hollow shelves. These containers may include vials with stoppers, ampoules, syringes, or, in the case of bulk lyophilization, pans.

The illustrated freeze-dryer unit 600 also includes a condenser 606 that is adapted to remove the sublimated and desorbed solvent from the vapor phase by condensing or freezing it out as ice to maintain adequate vacuum inside the freeze-dryer. The condenser 606 can be internally located in lyophilization chamber 602 or as a separate external unit in communication with the lyophilization chamber 602 through a so-called isolation valve. The freeze-dryer unit 600 also preferably includes a vacuum pump 608 operatively coupled to the condenser 606 and adapted to pull a vacuum on the lyophilization chamber 602 and condenser 606.

The cryogenic refrigeration system 610 provides the temperature control means for the freeze-dryer unit 600 by cooling a prescribed heat transfer fluid which is circulated to the shelves 604 within the lyophilization chamber 602 and the condenser 606. As illustrated, the cryogenic refrigeration system 610 comprises a source of cryogen 618, such as liquid nitrogen, a cryogenic heat exchanger 620, and a heat transfer fluid circuit 622, a vent 624, a heater 626 and pumps 627,628.

The cryogenic heat exchanger 620 is preferably an NCOOL™ Non-Freezing Cryogenic Heat Exchange System available from Praxair, Inc. An important aspect of the cryogenic heat exchanger 620 is the vaporization of the liquid nitrogen within or internal to the heat exchanger yet in a manner that avoids direct contact of the liquid nitrogen on cooling surfaces exposed to the heat transfer fluid. Details of the structure and operation of such a heat exchanger can be found in U.S. Pat. No. 5,937,656; the disclosure of which is incorporated by reference herein.

The prescribed heat transfer fluid circuit 622 is adapted to circulate a heat transfer fluid and is operatively coupled to both the lyophilization chamber 602 as well as the condenser 606. More specifically, the heat transfer fluid circulates inside the hollow shelves 604 within the lyophilization chamber 602 to precisely communicate the cooling or heating through the shelves 604 to the solution as needed. In addition the prescribed heat transfer fluid also flows through the condenser 606 to provide the cooling means necessary to sublimate the ice and further desorb the solvent.

Pump 627 and heater 626 are disposed along the heat transfer fluid circuit 622 upstream of the lyophilization chamber 602 and downstream of the cryogenic heat exchanger 620. The pump 627 is sized to move the heat transfer fluid through the heat transfer circuit 622 at the required flow rates. The heater 626 is preferably an electric heater adapted to provide supplemental heat to the heat transfer fluid and the lyophilization chamber 602 as may be required during the drying processes.

As seen in the embodiment of FIG. 17, the condenser 606 is also cooled by a recirculation low temperature heat transfer fluid. Refrigeration of the heat transfer fluid flowing through the condenser 606 is also provided by a cryogenic heat exchanger 620. The cryogenic heat exchanger 620 is capable of cooling heat transfer fluid continuously without freezing. During the drying phases, the cryogenic heat exchanger 620 is set or adapted to achieve the lowest temperature required for the condenser 606. As described above, the cryogenic heat exchanger 620 pre-evaporates liquid nitrogen into a cryogenic cold gas for heat transfer to the heat transfer fluid. Through pre-evaporation of the liquid nitrogen assures the liquid nitrogen avoids boiling off directly over a heat exchange surface where the heat transfer fluid is disposed on the other side. Such arrangement avoids freezing of the cryogenic heat exchanger 620 since liquid nitrogen boils at about −195 degrees Centigrade at atmospheric pressure.

The illustrated embodiment of FIG. 17 also includes a means for controlling the gas atmosphere of the lyophilization chamber 650, and in particular the gas composition and pressure within the chamber 602. Controlling the pressure of the chamber 602 allows for the pressurization and rapid depressurization of the chamber to induce nucleation of the solution. The disclosed embodiment preferably uses one or more flow control valves 652 controllably adapted to facilitate the introduction of a pressurized gas atmosphere to the chamber 602 from a source of gas (not shown) and to depressurize the chamber by venting the pressurized gas atmosphere away from the chamber 602 in a controlled and preferably rapid manner thereby inducing the nucleation of the solution in the various containers or vials.

Although not shown, the freeze-dryer unit 600 also includes various control hardware and software systems adapted to command and coordinate the various parts of the freeze-drying equipment, and carry out the pre-programmed lyophilization cycle. The various control hardware and software systems may also provide documentation, data logging, alarms, and system security capabilities as well. In addition, auxiliary systems to the freeze-dryer unit 600 may include various subsystems to clean and sterilize the lyophilization chamber 602, auto-load and unload the product in the lyophilization chamber 602; and associated cryogenic system accessories such as refrigeration skids, liquid nitrogen tanks, piping, valves, sensors, etc. Furthermore, the freeze-dryer unit 600 may be used optionally with or include the currently disclosed uniform flow controlled rate freezer system to cool and freeze the vials or containers in the system prior to initiating the freeze-drying process.

Figure 18A:
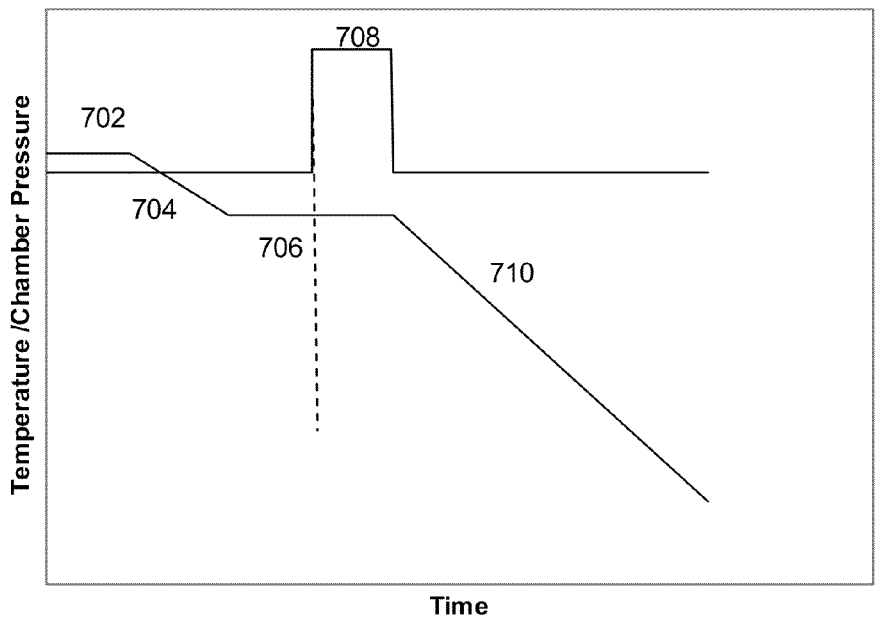
FIG. 18a depicts illustrative temperature and pressure profiles versus time of the cryogenic cold gas during a depressurization induced nucleation freezing process.

FIG. 18*a* presents a plot of an illustrative temperature and pressure profile versus time of the cryogenic cold gas during a depressurized nucleation freezing process as might be applied in the above disclosed cryogenic chiller, freeze-dryer unit, or other appropriate system. During equilibrium step 702 all vials in the chamber are brought to the same temperature prior to further cooling. During equilibrium step 702 the cooling chamber is preferably not actively pressurized. However the invention is not limited in this regards, in certain embodiments the cooling chamber may be pressurized above or below atmospheric pressure. After equilibrating all of the vials or containers to the same temperature the cryogenic cold gas is cooled at a predetermined rate to the pre-nucleation temperature (PNT) and held for a selected amount of time during steps 704 and 706. The vials cool in response to the decreased temperature of the cryogenic cold gas and approach the PNT. While the cryogenic cold gas is held at the PNT a pressurization and depressurization step 708 is applied. During pressurization and depressurization step 708, the chamber pressure is increased and held for a predetermined amount of time prior to depressurizing the system. Nucleation is induced by the depressurization. Alternatively, the prior steps could be conducted at a first pressure and nucleation can be induced by depressurizing the system to a lower second pressure without the need to pressurize the system. After nucleation is induced, the cryogenic cold gas is further cooled during step 710 to a desired final temperature (i.e. −80° C.) at various rates. Without wishing to be bound by theory it is believed that the nucleation control is relatively insensitive to the rate of pressurization. However, it is necessary to ensure that a sufficient pressure drop occurs over a short enough time period to induce nucleation. Furthermore, it will be necessary to determine optimal conditions for each new material to be frozen. Examples of testing regarding the above discussed nucleation process is provided below.

Figure 18B:
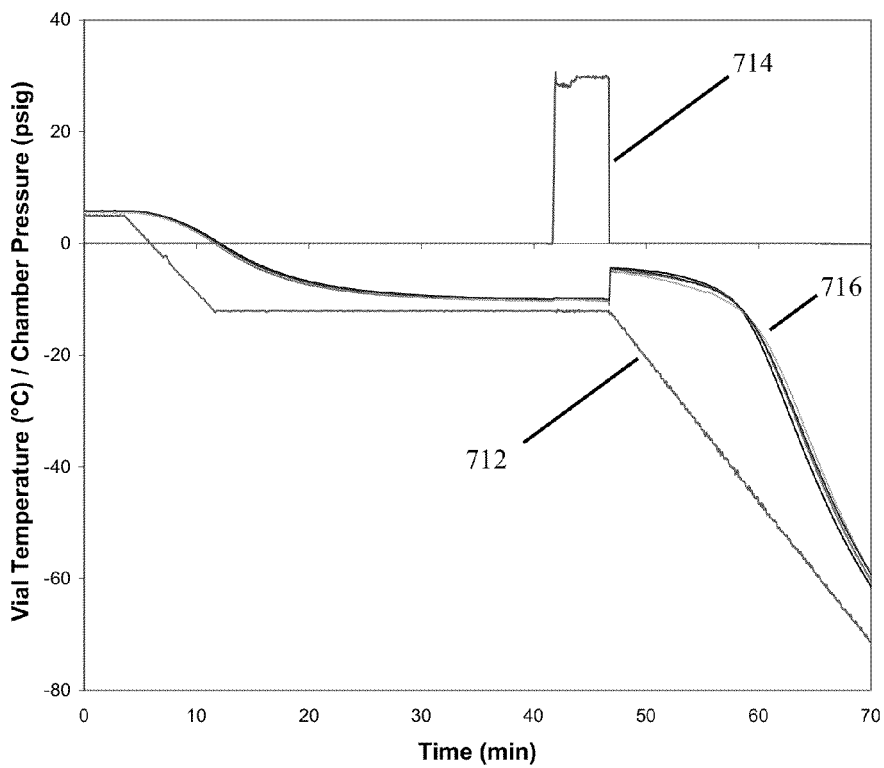
FIG. 18b is a graph depicting the pressure profile and the temperature profiles of different samples during a depressurization induced nucleation freezing process.

FIG. 18*b* presents temperature and pressure profiles for samples undergoing the process described above in connection with FIG. 18*a*. Four separate 2 ml vials were filled with 1 ml of phosphate buffered saline and 10 (v/v) % Dimethyl sulfoxide (DMSO) solution. The four vials were then placed in randomly selected spaced apart locations on a tray. The tray was then placed into a uniform flow cryogenic chiller with pressure control. The temperatures of the four vials were monitored using the thermocouples placed inside the liquid contained in each vial. The cryogenic cold gas temperature profile 712 and chamber pressure profile 714 were then applied to freeze the four vials. The chamber pressure was raised to 30 psig and held at 30 psig for 5 min prior to depressurization. The sharp temperature rise in vial temperatures 716 after depressurization indicates that all four vials nucleated and began freezing immediately after depressurization. The vial temperatures 716 were substantially uniform for the four samples throughout the freezing process.

Turning again to FIGS. 12 and 18*b*, these figures provide an example of sample container temperatures prior to and after nucleation of the material during a freezing process. The differences in temperature between the samples are greater after nucleation. This change in uniformity of the temperature is due to the latent heat of freezing being slightly different for each sample since each sample nucleates at a slightly different temperature. Thus since each sample has a different latent heat of freezing and each sample starts at a slightly different temperature, the resulting differences in temperature sample-to-sample are larger after nucleation.

In one embodiment, the uniformity of the container temperatures are maintained within ±2.5° C. of each other during a freezing process, prior to nucleation, regardless of a location in the cooling chamber where the material is frozen. After nucleation, the uniformity of the container temperatures may be maintained within ±5° C. of each other during the remainder of the freezing process regardless of a location in the cooling chamber where the material is frozen. In another embodiment, the uniformity of the container temperatures are maintained within the measurement error of thermocouple during a freezing process, prior to nucleation, regardless of a location in the cooling chamber where the material is frozen. Typical measurement errors are on the order of ±1° C. After nucleation, the uniformity of the container temperatures may be maintained within ±2.5° C. of each other during the remainder of the freezing process regardless of a location in the cooling chamber where the material is frozen. The above examples of temperature uniformity prior to and after nucleation are non-limiting with respect to the current disclosure.

As seen in FIGS. 12, 15, 16, and 18b nucleation may be induced using either the above described temperature quench or pressure induced nucleation control methods. Nucleation occurs over a smaller time period as compared to the stochastic nucleation processes presented in FIGS. 13 and 14. Furthermore, the above described uniform controlled rate freezer may be adapted to implement either, or both, the temperature quench and pressure induced nucleation methods to selectively induce nucleation substantially at the same time in each sample. Therefore, the current systems may provide a substantially uniform nucleation time and temperature for each sample regardless of location within the cooling chamber.

In addition to the above, FIGS. 13 and 14 specifically show the differences between a stochastic nucleation process using the currently disclosed uniform flow cryogenic chiller and a stochastic nucleation process using a prior art system. As illustrated in the figures the samples nucleated over a smaller temperature range in the uniform flow cryogenic chiller as compared to the prior art system. Without wishing to be bound by theory, this difference in the uniformity of the stochastic nucleation temperatures may be due to the uniform temperature of the cryogenic cold gas applied to the samples in the uniform flow cryogenic chiller. Therefore, in one embodiment, the currently disclosed uniform flow cryogenic chiller may provide a uniform stochastic nucleation temperature to a plurality of containers. In a further embodiment, a stochastic nucleation temperature may be provided to 10,000, 20,000, 50,000, or 100,000 containers in the same system.

It should be noted that the current invention is not limited to the specific temperature and pressure profiles described herein. Any number of variations of the described freezing and nucleation processes will be apparent to one of skill in the art and can be implemented without departing from the spirit of the current disclosure.

Depressurized Nucleation Examples

The following examples highlight various aspects and features of the presently disclosed method of inducing nucleation via pressure control in a material and are not to be taken in a limiting sense. Rather, these examples are illustrative only and the scope of the invention should be determined only with respect to the claims, appended hereto.

All examples described herein were performed in a pilot-scale VirTis 51-SRC freeze-dryer having four shelves with approximately 1.0 square meter total shelf space and an internal condenser. This unit was retrofitted to hold positive pressures of up to about 15 psig. A 1.5" diameter circular opening also was added to the rear wall of the freeze-drying chamber with 1.5" diameter stainless steel tubing extending from the hole through the rear wall insulation to emerge from the back of the freeze-dryer. Two 1.5" full-port, air-actuated ball valves were attached to this tubing via sanitary fittings. One ball valve allowed gas to flow into the freeze-drying chamber and thereby provide positive pressures up to 15 psig. The second ball valve allowed gas to flow out of the freeze-drying chamber and thereby reduce chamber pressure to atmospheric conditions (0 psig). All refrigeration of the freeze-dryer shelves and condenser was accomplished via circulation of Dynalene MV heat transfer fluid cooled by liquid nitrogen using the Praxair NCool™-HX system.

All solutions were prepared in a class 100 clean room. The freeze-dryer was positioned with the door, shelves, and controls all accessible from the clean room while the other components (pumps, heaters, etc.) were located in a non-clean room environment. All solutions were prepared with HPLC grade water (Fisher Scientific, filtered through 0.10 μm membrane). The final solutions were filtered through a 0.22 μm membrane prior to filling the vials or lyophilization containers. All gases were supplied via cylinders and were filtered through 0.22 μm filters to remove particulates. The glass containers (5 mL vials and 60 mL bottles) were obtained pre-cleaned for particulates from Wheaton Science Products. Pharmaceutically acceptable carriers were used where appropriate. The above steps were taken to ensure the materials and methods met conventional pharmaceutical manufacturing standards for particulates, which act as nucleating agents.

As used herein, "pharmaceutically acceptable carrier" includes any and all solvents, dispersion media, antioxidants, salts, coatings, surfactants, preservatives (e.g., methyl or propyl p-hydroxybenzoate, sorbic acid, antibacterial agents, antifungal agents), isotonic agents, solution retarding agents (e.g., paraffin), absorbents (e.g., kaolin clay, bentonite clay), drug stabilizers (e.g., sodium lauryl sulphate), gels, binders (e.g., syrup, acacia, gelatin, sorbitol, tragacanth, polyvinyl pyrrolidone, carboxy-methyl-cellulose, alginates), excipients (e.g., lactose, milk sugar, polyethylene glycol), disintegration agent (e.g., agar-agar, starch, lactose, calcium phosphate, calcium carbonate, alginic acid, sorbitol, glycine), wetting agents (e.g., cetyl alcohol, glycerol monostearate), lubricants, absorption accelerators (e.g., quaternary ammonium salts), edible oils (e.g., almond oil, coconut oil, oily esters or propylene glycol), sweetening agents, flavoring agents, coloring agents, fillers, (e.g., starch, lactose, sucrose, glucose, mannitol), tabletting lubricants (e.g., magnesium stearate, starch, glucose, lactose, rice flower, chalk), carriers for inhalation (e.g., hydrocarbon propellants), buffering agents, or such like materials and combinations thereof, as would be known to one of ordinary skill in the art.

For the experimental conditions described herein and all lyophilization formulations studied, stochastic nucleation was typically observed to occur at container temperatures between about −8° C. and −20° C. and occasionally as warm as −5° C. The containers could generally be held at temperatures warmer than −8° C. for long periods of time without nucleating. The onset of nucleation and subsequent crystal growth (i.e., freezing) was determined by temperature measurement as the point at which the container temperature quickly increased in response to the exothermic latent heat of fusion. The initiation of freezing also could be visually determined through a sight-glass on the freeze-dryer chamber door.

Example 1

Controlling the Nucleation Temperature

Four separate vials were filled with 2.5 mL of 5 wt % mannitol solution. The predicted thermodynamic freezing point of the 5 wt % mannitol solution is approximately −0.5° C. The four vials were placed on a freeze-dryer shelf in close proximity to one another. The temperatures of the four vials were monitored using surface mounted thermocouples. The freeze-dryer was pressurized with argon to 14 psig.

The freeze-dryer shelf was cooled to obtain vial temperatures of between approximately −1.3° C. and about −2.3° C. (±1° C. measurement accuracy of the thermocouples). The freeze-dryer was then depressurized from about 14 psig to about atmospheric pressure in less than five seconds to induce nucleation of the solution within the vials. All four vials nucleated and began freezing immediately after depressurization. Results are summarized in Table 1 below.

As seen in Table 1, the controlled nucleation temperatures in this example (i.e., Initial Vial Temperatures) are quite close to the predicted thermodynamic freezing point of the solution. Thus the present method allows control of the nucleation to occur in solutions that have a very low degree of sub-cooling or at nucleation temperatures near or only slightly colder than their freezing points.

TABLE 1

Controlling the Nucleation Temperature

| Vial # | Solution | Atmos | Initial Vial Temperature [° C.] | Pressure Drop [psi] | Depressurization Outcome |
|---|---|---|---|---|---|
| 1 | 2.5 mL of 5 wt % mannitol | Argon | −2.3 | 14 | Nucleation |
| 2 | 2.5 mL of 5 wt % mannitol | Argon | −1.3 | 14 | Nucleation |
| 3 | 2.5 mL of 5 wt % mannitol | Argon | −2.1 | 14 | Nucleation |
| 4 | 2.5 mL of 5 wt % mannitol | Argon | −1.7 | 14 | Nucleation |

Example 2

Controlling the Nucleation Temperature

In this example, ninety-five vials were filled with 2.5 mL of 5 wt % mannitol solution. The thermodynamic freezing point of the 5 wt % mannitol solution is approximately −0.5° C. The ninety-five vials were placed on a freeze-dryer shelf in close proximity to one another. The temperatures of six vials positioned at different locations in the freeze-dryer shelf were continuously monitored using surface mounted thermocouples. The freeze-dryer was pressurized in an argon atmosphere to about 14 psig. The freeze-dryer shelf was then cooled to obtain vial temperatures of near −5° C. The freeze-dryer was then depressurized from about 14 psig to about atmospheric pressure in less than five seconds to induce nucleation of the solution within the vials. All ninety-five vials were visually observed to nucleate and begin freezing immediately after depressurization. Thermocouple data for the six monitored vials confirmed the visual observation. The results are summarized in Table 2.

As seen therein, controlled nucleation temperatures in this example (i.e., Initial Vial Temperatures) are somewhat below the predicted thermodynamic freezing point of the solution. Thus the present method allows control of the nucleation to occur in solutions that have a moderate degree of sub-cooling. This example also demonstrates scalability of the present method to a multiple vial application.

TABLE 2

Controlling the Nucleation Temperature

| Vial # | Solution | Atmos | Initial Vial Temperature [° C.] | Pressure Drop [psi] | Depressurization Outcome |
|---|---|---|---|---|---|
| 1 | 2.5 mL of 5 wt % mannitol | Argon | −4.2 | 14 | Nucleation |
| 2 | 2.5 mL of 5 wt % mannitol | Argon | −4.4 | 14 | Nucleation |
| 3 | 2.5 mL of 5 wt % mannitol | Argon | −4.6 | 14 | Nucleation |
| 4 | 2.5 mL of 5 wt % mannitol | Argon | −4.4 | 14 | Nucleation |
| 5 | 2.5 mL of 5 wt % mannitol | Argon | −4.6 | 14 | Nucleation |
| 6 | 2.5 mL of 5 wt % mannitol | Argon | −5.1 | 14 | Nucleation |

Example 3

Controlling the Depressurization Magnitude

In this example, multiple vials were filled with 2.5 mL of 5 wt % mannitol solution. Again, the predicted thermodynamic freezing point of the 5 wt % mannitol solution is approximately −0.5° C. For each test run, the vials were placed on a freeze-dryer shelf in close proximity to one another. As with the earlier described examples, the temperatures of vials were monitored using surface mounted thermocouples. The argon atmosphere in the freeze-dryer was pressurized to differing pressures and the freeze-dryer shelf was cooled to obtain vial temperatures of about −5° C. In each test run, the freeze-dryer was then rapidly depressurized (i.e., in less than five seconds) from the selected pressure to atmospheric pressure in an effort to induce nucleation of the solution within the vials. Results are summarized in Table 3.

As seen in Table 3, the controlled nucleation occurred where the pressure drop was about 7 psi or greater and the nucleation temperature (i.e., initial vial temperature) was between about −4.7° C. and −5.8° C.

TABLE 3

Effect of Depressurization Magnitude

| Vial # | Solution | Atmos | Initial Vial Temperature [° C.] | Pressure Drop [psi] | Depressurization Outcome |
|---|---|---|---|---|---|
| 1 | 2.5 mL of 5 wt % mannitol | Argon | −4.7 | 7 | Nucleation |
| 2 | 2.5 mL of 5 wt % mannitol | Argon | −5.1 | 7 | Nucleation |
| 3 | 2.5 mL of 5 wt % mannitol | Argon | −5.3 | 7 | Nucleation |
| 4 | 2.5 mL of 5 wt % mannitol | Argon | −5.6 | 7 | No Nucleation |

TABLE 3-continued

Effect of Depressurization Magnitude

| Vial # | Solution | Atmos | Initial Vial Temperature [° C.] | Pressure Drop [psi] | Depressurization Outcome |
|---|---|---|---|---|---|
| 5 | 2.5 mL of 5 wt % mannitol | Argon | −5.6 | 7 | Nucleation |
| 6 | 2.5 mL of 5 wt % mannitol | Argon | −5.8 | 7 | Nucleation |
| 7 | 2.5 mL of 5 wt % mannitol | Argon | −5.4 | 6 | No Nucleation |
| 8 | 2.5 mL of 5 wt % mannitol | Argon | −5.7 | 6 | No Nucleation |
| 9 | 2.5 mL of 5 wt % mannitol | Argon | −5.8 | 6 | No Nucleation |
| 10 | 2.5 mL of 5 wt % mannitol | Argon | −5.1 | 5 | No Nucleation |
| 11 | 2.5 mL of 5 wt % mannitol | Argon | −5.4 | 5 | No Nucleation |
| 12 | 2.5 mL of 5 wt % mannitol | Argon | −5.5 | 5 | No Nucleation |
| 13 | 2.5 mL of 5 wt % mannitol | Argon | −4.7 | 4 | No Nucleation |
| 14 | 2.5 mL of 5 wt % mannitol | Argon | −5.1 | 4 | No Nucleation |
| 15 | 2.5 mL of 5 wt % mannitol | Argon | −5.3 | 4 | No Nucleation |

Example 4

Controlling the Depressurization Rates

For this example, multiple vials were filled with about 2.5 mL of 5 wt % mannitol solution having a predicted thermodynamic freezing point of approximately −0.5° C. For each test run of varying depressurization time, the vials were placed on a freeze-dryer shelf in close proximity to one another. As with the earlier described examples, the temperatures of vials were monitored using surface mounted thermocouples. Like the above-described examples, the argon atmosphere in the freeze-dryer was pressurized to about 14 psig and the shelf was cooled to obtain vial temperatures of approximately −5° C. In each test run, the freeze-dryer was then depressurized at different depressurization rates from 14 psig to atmospheric pressure in an effort to induce nucleation of the solution within the vials.

To study the effect of depressurization rate or depressurization time, a restricting ball valve was placed on the outlet of the depressurization control valve at the rear of the freeze-dryer. When the restricting valve is completely open, depressurization from about 14 psig to about 0 psig is accomplished in approximately 2.5 seconds. By only partially closing the restricting valve, it is possible to variably increase the chamber depressurization time. Using the restricting ball valve, several test runs were performed with the freeze-dryer chamber depressurized at differing rates to ascertain or determine the effect of depressurization rate on nucleation. The results are summarized in Table 4.

TABLE 4

Effect of Depressurization Time

| Vial # | Solution | Atmos | Vial Temp [° C.] | Pressure Drop [psi] | Time [sec] | Depressurization Outcome |
|---|---|---|---|---|---|---|
| 1 | 2.5 mL of 5 wt % mannitol | Argon | −4.6 | 14 | 300 | No Nucleation |
| 2 | 2.5 mL of 5 wt % mannitol | Argon | −5.4 | 14 | 300 | No Nucleation |
| 3 | 2.5 mL of 5 wt % mannitol | Argon | −5.8 | 14 | 300 | No Nucleation |
| 4 | 2.5 mL of 5 wt % mannitol | Argon | −4.6 | 14 | 200 | No Nucleation |
| 5 | 2.5 mL of 5 wt % mannitol | Argon | −5.4 | 14 | 200 | No Nucleation |
| 6 | 2.5 mL of 5 wt % mannitol | Argon | −5.4 | 14 | 200 | No Nucleation |
| 7 | 2.5 mL of 5 wt % mannitol | Argon | −4.6 | 14 | 100 | No Nucleation |
| 8 | 2.5 mL of 5 wt % mannitol | Argon | −5.2 | 14 | 100 | No Nucleation |
| 9 | 2.5 mL of 5 wt % mannitol | Argon | −5.2 | 14 | 100 | No Nucleation |
| 10 | 2.5 mL of 5 wt % mannitol | Argon | −4.7 | 14 | 60 | No Nucleation |
| 11 | 2.5 mL of 5 wt % mannitol | Argon | −5.1 | 14 | 60 | No Nucleation |
| 12 | 2.5 mL of 5 wt % mannitol | Argon | −5.1 | 14 | 60 | No Nucleation |
| 13 | 2.5 mL of 5 wt % mannitol | Argon | −5.1 | 14 | 50 | No Nucleation |
| 14 | 2.5 mL of 5 wt % mannitol | Argon | −5.3 | 14 | 50 | No Nucleation |
| 15 | 2.5 mL of 5 wt % mannitol | Argon | −4.9 | 14 | 50 | No Nucleation |
| 16 | 2.5 mL of 5 wt % mannitol | Argon | −5.4 | 14 | 42 | No Nucleation |
| 17 | 2.5 mL of 5 wt % mannitol | Argon | −5.5 | 14 | 42 | No Nucleation |
| 18 | 2.5 mL of 5 wt % mannitol | Argon | −5.0 | 14 | 42 | No Nucleation |
| 19 | 2.5 mL of 5 wt % mannitol | Argon | −5.1 | 14 | 32 | Nucleation |
| 20 | 2.5 mL of 5 wt % mannitol | Argon | −5.7 | 14 | 32 | Nucleation |
| 21 | 2.5 mL of 5 wt % mannitol | Argon | −5.6 | 14 | 32 | Nucleation |
| 22 | 2.5 mL of 5 wt % mannitol | Argon | −4.7 | 14 | 13 | Nucleation |
| 23 | 2.5 mL of 5 wt % mannitol | Argon | −5.3 | 14 | 13 | Nucleation |
| 24 | 2.5 mL of 5 wt % mannitol | Argon | −5.5 | 14 | 13 | Nucleation |

As seen in Table 4, nucleation only occurred where the depressurization time was less than 42 seconds, the pressure drop was about 14 psi or greater and the nucleation temperature (i.e., initial vial temperature) was between about −4.6° C. and about −5.8° C. These results indicate that the depressurization needs to be accomplished relatively quickly for the method to be effective.

Example 5

Controlling the Gas Atmosphere

Again, multiple vials were each filled with about 2.5 mL of 5 wt % mannitol solution and placed on a freeze-dryer shelf in close proximity to one another. As with earlier described examples, temperature of the test vials were monitored using surface mounted thermocouples. For the different test runs, the gas atmosphere in the freeze-dryer was varied always maintaining a positive pressure of about 14 psig. In this example, the freeze-dryer shelf was cooled to obtain vial temperatures of approximately −5° C. to −7° C. In each test run, the freeze-dryer was then rapidly depressurized from about 14 psig to atmospheric pressure in an effort to induce nucleation of the solution within the vials. The results are summarized in Table 5.

As seen therein, controlled nucleation occurred in all gas atmospheres except for helium gas atmosphere where the pressure drop was about 14 psi and the nucleation temperature (i.e., initial vial temperature) was between about −4.7° C. and about −7.4° C. Although not shown in the examples, it is believed that alternate conditions will likely enable controlled nucleation in a helium atmosphere.

TABLE 5

Effect of Gas Atmosphere Composition

| Vial # | Solution | Atmos | Initial Vial Temp [° C.] | Pressure Drop [psi] | Depressurization Outcome |
|---|---|---|---|---|---|
| 1 | 2.5 mL of 5 wt % mannitol | Argon | −4.9 | 14 | Nucleation |
| 2 | 2.5 mL of 5 wt % mannitol | Argon | −5.2 | 14 | Nucleation |
| 3 | 2.5 mL of 5 wt % mannitol | Nitrogen | −4.7 | 14 | Nucleation |
| 4 | 2.5 mL of 5 wt % mannitol | Nitrogen | −5.1 | 14 | Nucleation |
| 5 | 2.5 mL of 5 wt % mannitol | Xenon | −4.8 | 14 | Nucleation |
| 6 | 2.5 mL of 5 wt % mannitol | Xenon | −5.0 | 14 | Nucleation |
| 7 | 2.5 mL of 5 wt % mannitol | Air | −7.4 | 14 | Nucleation |
| 8 | 2.5 mL of 5 wt % mannitol | Air | −7.2 | 14 | Nucleation |
| 9 | 2.5 mL of 5 wt % mannitol | Helium | −5.8 | 14 | No Nucleation |
| 10 | 2.5 mL of 5 wt % mannitol | Helium | −5.5 | 14 | No Nucleation |

Example 6

Large Volume Solutions

In this example, six lyophilization bottles (60 mL capacity) were filled with about 30 mL of 5 wt % mannitol solution having a predicted thermodynamic freezing point of approximately −0.5° C. The six lyophilization bottles were placed on a freeze-dryer shelf in close proximity to one another. The temperature of six bottles positioned at different locations in the freeze-dryer shelf was monitored using surface mounted thermocouples. The freeze-dryer was pressurized in an argon atmosphere to about 14 psig. The freeze-dryer shelf was then cooled to obtain bottle temperatures of near −5° C. The freeze-dryer was then depressurized from 14 psig to about atmospheric pressure in less than five seconds to induce nucleation of the solution within the bottles. The results are summarized in Table 6.

In a separate experiment, a plastic bulk freeze-drying tray (Gore LYOGUARD, 1800 mL capacity) was filled with about 1000 mL of 5 wt % mannitol solution. The tray was obtained pre-cleaned to meet USP low particulate requirements. The tray was placed on a freeze-dryer shelf, and the temperature of the tray was monitored by a thermocouple mounted on the exterior surface of the tray near the center of one side. The freeze-dryer shelf was then cooled to obtain a tray temperature of near −7° C. The freeze-dryer was then depressurized from 14 psig to about atmospheric pressure in less than five seconds to induce nucleation of the solution within the tray. The results are also summarized in Table 6.

Like the above-described examples, all containers nucleated and began freezing immediately after depressurization. Also like the above-described examples, the nucleation temperatures (i.e., Container Temperatures) in this example were very much controllable to be somewhat near the thermodynamic freezing temperature of the solution. More importantly, this example illustrates that the present method allows control of the nucleation to occur in larger volume solutions and various container formats. It should be noted that one would expect the efficacy of the depressurization method to improve as formulation volume increases, because the nucleation event is more likely to occur when more molecules are present to aggregate and form critical nuclei.

TABLE 6

Effect of Solution Volume and Container Type

| Container | Solution | Atmos | Container Temperature [° C.] | Pressure Drop [psi] | Depressurization Outcome |
|---|---|---|---|---|---|
| Bottle # 1 | 30 mL of 5 wt % mannitol | Argon | −5.3 | 14 | Nucleation |
| Bottle # 2 | 30 mL of 5 wt % mannitol | Argon | −5.1 | 14 | Nucleation |

TABLE 6-continued

Effect of Solution Volume and Container Type

| Container | Solution | Atmos | Container Temperature [° C.] | Pressure Drop [psi] | Depressurization Outcome |
|---|---|---|---|---|---|
| Bottle # 3 | 30 mL of 5 wt % mannitol | Argon | −5.9 | 14 | Nucleation |
| Bottle # 4 | 30 mL of 5 wt % mannitol | Argon | −5.2 | 14 | Nucleation |
| Bottle # 5 | 30 mL of 5 wt % mannitol | Argon | −5.9 | 14 | Nucleation |
| Bottle # 6 | 30 mL of 5 wt % mannitol | Argon | −6.1 | 14 | Nucleation |
| Tray | 1000 mL of 5 wt % mannitol | Argon | −6.9 | 14 | Nucleation |

Example 7

Dynamic Cooling Vs. Equilibrated Cooling

The present methods of controlling nucleation can be used in various modes. Examples 1-6, described above, each demonstrate the aspect of controlling the nucleation temperature of a lyophilization solution that is essentially equilibrated at a temperature below its thermodynamic freezing point (i.e., very slowly changing temperature). This example demonstrates that nucleation can also occur at a temperature below the thermodynamic freezing point in a dynamic cooling environment (i.e., the solution is undergoing rapid changes in temperature).

In this example, vials 1 through 6 represent the samples described above with reference to Example 2. In addition, three separate vials (Vials 7-9) were also filled with 2.5 mL of 5 wt % mannitol solution. In a separate test run, the three additional vials were placed on a freeze-dryer shelf in close proximity to one another. The freeze-dryer shelf was cooled rapidly towards a final shelf temperature of −45° C. When one of the vials reached a temperature of about −5° C., as measured by the surface mounted thermocouples, the freeze-dryer was depressurized rapidly from about 14 psig to 0 psig in an effort to induce nucleation. All three vials nucleated and began freezing immediately after depressurization. The vial temperatures decreased significantly to between −6.8° C. and −9.9° C. prior to nucleation as a result of the dynamic cooling environment. Comparative results are summarized in Table 7 below.

TABLE 7

Test Results - Effect of Dynamic Cooling on Nucleation

| Vial # | Solution | Mode | Nucleation Temp. [° C.] | Pressure Drop [psi] | Depressurization Outcome |
|---|---|---|---|---|---|
| 1 | 2.5 mL of 5 wt % mannitol | Equilibrated | −4.2 | 14 | Nucleation |
| 2 | 2.5 mL of 5 wt % mannitol | Equilibrated | −4.4 | 14 | Nucleation |
| 3 | 2.5 mL of 5 wt % mannitol | Equilibrated | −4.6 | 14 | Nucleation |
| 4 | 2.5 mL of 5 wt % mannitol | Equilibrated | −4.4 | 14 | Nucleation |
| 5 | 2.5 mL of 5 wt % mannitol | Equilibrated | −4.6 | 14 | Nucleation |
| 6 | 2.5 mL of 5 wt % mannitol | Equilibrated | −5.1 | 14 | Nucleation |
| 7 | 2.5 mL of 5 wt % mannitol | Dynamic | −6.8 | 14 | Nucleation |
| 8 | 2.5 mL of 5 wt % mannitol | Dynamic | −7.2 | 14 | Nucleation |
| 9 | 2.5 mL of 5 wt % mannitol | Dynamic | −9.9 | 14 | Nucleation |

The efficacy of the present methods for controlling nucleation in lyophilization solutions equilibrated in a given temperature range or lyophilization solutions being dynamically cooled, provides the end-user with two potential modes of application with different benefits and trade-offs. By allowing the lyophilization solutions to equilibrate, the range of nucleation temperatures will be narrow or minimized to the performance limits of the freeze-dryer itself. The equilibration step may require extra time to achieve relative to conventional or dynamic freezing protocols where the chamber and vial temperatures are dropped to less than about −40° C. in one step. However, employing the equilibration step should yield much improved nucleation uniformity across all vials or containers as well as realization of the other benefits associated with precisely controlling the nucleation temperature of the material.

Alternatively, if equilibrating the material or lyophilization solution temperatures is undesirable, one may simply implement the depressurization step at an appropriate time during the normal freezing or dynamic cooling protocol. Depressurization during a dynamic cool down will produce a wider spread in nucleation temperatures for the material within the lyophilization containers, but will add minimal time to the freezing protocol and still allow one to mitigate the problems of extreme sub-cooling.

Example 8

Effect of Different Excipients

The present method of controlling or inducing nucleation in a material can be used to control the nucleation temperature of sub-cooled solutions containing different lyophilization excipients. This example demonstrates the use of the present methods with the following excipients: mannitol; hydroxyethyl starch (HES); polyethylene glycol (PEG); polyvinyl pyrrolidone (PVP); dextran; glycine; sorbitol; sucrose; and trehalose. For each excipient, two vials were filled with 2.5 mL of a solution containing 5 wt % of the excipient. The vials were placed on a freeze-dryer shelf in close proximity to one another. The freeze-dryer was pressurized in an argon atmosphere to about 14 psig. The freeze-dryer shelf was cooled to obtain vial temperatures near −3° C. and then depressurized rapidly to induce nucleation. Results are summarized in Table 8.

TABLE 8

Effect of Different Lyophilization Excipients

| Vial # | Solution/Excipient | Atmos | Initial Vial Temperature [° C.] | Pressure Drop [psi] | Depressurization Outcome |
|---|---|---|---|---|---|
| 1 | 2.5 mL of 5 wt % mannitol | Argon | −3.3 | 14 | Nucleation |
| 2 | 2.5 mL of 5 wt % mannitol | Argon | −3.0 | 14 | Nucleation |
| 3 | 2.5 mL of 5 wt % HES | Argon | −3.1 | 14 | Nucleation |
| 4 | 2.5 mL of 5 wt % HES | Argon | −3.7 | 14 | Nucleation |
| 5 | 2.5 mL of 5 wt % PEG | Argon | −3.8 | 14 | Nucleation |
| 6 | 2.5 mL of 5 wt % PEG | Argon | −3.4 | 14 | Nucleation |
| 7 | 2.5 mL of 5 wt % PVP | Argon | −3.5 | 14 | Nucleation |
| 8 | 2.5 mL of 5 wt % PVP | Argon | −3.3 | 14 | Nucleation |
| 9 | 2.5 mL of 5 wt % dextran | Argon | −4.0 | 14 | Nucleation |
| 10 | 2.5 mL of 5 wt % dextran | Argon | −3.1 | 14 | Nucleation |
| 11 | 2.5 mL of 5 wt % glycine | Argon | −3.8 | 14 | Nucleation |
| 12 | 2.5 mL of 5 wt % glycine | Argon | −3.9 | 14 | Nucleation |
| 13 | 2.5 mL of 5 wt % sorbitol | Argon | −3.6 | 14 | Nucleation |
| 14 | 2.5 mL of 5 wt % sorbitol | Argon | −3.4 | 14 | Nucleation |
| 15 | 2.5 mL of 5 wt % sucrose | Argon | −3.3 | 14 | Nucleation |
| 16 | 2.5 mL of 5 wt % sucrose | Argon | −3.4 | 14 | Nucleation |
| 17 | 2.5 mL of 5 wt % trehalose | Argon | −3.7 | 14 | Nucleation |
| 18 | 2.5 mL of 5 wt % trehalose | Argon | −3.1 | 14 | Nucleation |

Example 9

Controlling Nucleation of Protein Solutions

The methods disclosed herein can be used to control the nucleation temperature of sub-cooled protein solutions without negative or adverse effects on protein solubility or enzymatic activity. Two proteins, bovine serum albumin (BSA) and lactate dehydrogenase (LDH) were used in this example.

BSA was dissolved in 5 wt % mannitol at a concentration of 10 mg/mL. Three lyophilization vials were filled with 2.5 mL of the BSA-mannitol solution and placed on a freeze-dryer shelf in close proximity to one another. The freeze-dryer was pressurized in an argon atmosphere to about 14 psig. The freeze-dryer shelf was cooled to obtain vial temperatures near −5° C. The freeze-dryer was depressurized rapidly to induce nucleation. All vials of BSA solution nucleated and began freezing immediately after depressurization. No precipitation of the protein was observed upon thawing.

The LDH proteins were obtained from two different suppliers and for purposes of clarity are designated as LDH-1 or LDH-2 to distinguish the two distinct batches. LDH-1 was dissolved in 5 wt % mannitol at a concentration of 1 mg/mL. Six lyophilization vials were filled with 2.5 mL of the LDH-1/mannitol solution and placed on a freeze-dryer shelf in close proximity to one another. The freeze-dryer was pressurized in an argon atmosphere to about 14 psig. The freeze-dryer shelf was cooled starting from room temperature to obtain vial temperatures near −4° C. The freeze-dryer was then depressurized rapidly to induce nucleation. All vials nucleated and began freezing immediately after depressurization. The vials were held at this state for about 15 minutes. The freeze-dryer shelf was then cooled at a rate of approximately 1° C./min to obtain vial temperatures near −45° C. and held for an additional 15 minutes to ensure completion of the freezing process. After the freezing step, the freeze-dryer shelf was then warmed at a rate of about 1° C./min to raise the vial temperatures to near 5° C. No precipitation of the protein was observed upon thawing. The vial contents were assayed for enzymatic activity, and the results were compared to a control sample of unfrozen LDH-1/mannitol solution.

As part of Example 9, the depressurized nucleated samples of the LDH-1/mannitol solution were compared to stochastically nucleated samples. In the stochastically nucleated samples of LDH-1, the freezing procedure was repeated without pressurization and depressurization and without the argon atmosphere. Specifically, LDH-1 was dissolved in 5 wt % mannitol at a concentration of 1 mg/mL. Six lyophilization vials were filled with 2.5 mL of the LDH-1/mannitol solution and placed on a freeze-dryer shelf in close proximity to one another. The freeze-dryer shelf was cooled starting from room temperature at a rate of about 1° C./min to obtain vial temperatures near −45° C. and held for 15 minutes to ensure completion of the freezing process. After the freezing step, the freeze-dryer shelf was warmed at a rate of about 1° C./min to raise the vial temperatures to near 5° C. No precipitation of the protein was observed upon thawing. The vial contents were assayed for enzymatic activity, and the results were compared to the same control sample of unfrozen LDH-1/mannitol solution. Also as part of Example 9, the experiments described above for LDH-1 were repeated using LDH-2. The only difference was a nucleation temperature near −3° C. for LDH-2 rather than −4° C. for LDH-1.

As seen in Table 9, the controlled nucleation and freezing process achieved via depressurization clearly does not decrease enzymatic activity relative to a comparable stochastic nucleation and freezing protocol. In fact, the controlled nucleation process achieved via depressurization appears to better preserve enzyme activity with a mean activity loss of only 17.8% for LDH-1 and 26.5% for LDH-2 compared to the mean activity loss of 35.9% for LDH-1 and 41.3% for LDH-2 after stochastic nucleation.

TABLE 9

Controlling the Nucleation Temperature of Sub-Cooled Protein Solutions

| Vial # | Solution | Atmos | Initial Vial Temp [° C.] | Pressure Drop [psi] | Enzyme Activity Loss [%] | Depressurization Outcome |
|---|---|---|---|---|---|---|
| 1 | 2.5 mL of BSA solution | Argon | −4.9 | 14 | — | Nucleation |
| 2 | 2.5 mL of BSA solution | Argon | −4.3 | 14 | — | Nucleation |
| 3 | 2.5 mL of BSA solution | Argon | −5.3 | 14 | — | Nucleation |
| 4 | 2.5 mL of LDH-1 solution | Argon | −3.8 | 14 | 9.0 | Nucleation |
| 5 | 2.5 mL of LDH-1 solution | Argon | −4.0 | 14 | 16.2 | Nucleation |
| 6 | 2.5 mL of LDH-1 solution | Argon | −3.7 | 14 | 18.4 | Nucleation |
| 7 | 2.5 mL of LDH-1 solution | Argon | −4.0 | 14 | 23.4 | Nucleation |
| 8 | 2.5 mL of LDH-1 solution | Argon | −3.9 | 14 | 18.5 | Nucleation |
| 9 | 2.5 mL of LDH-1 solution | Argon | −4.0 | 14 | 21.2 | Nucleation |
| 10 | 2.5 mL of LDH-1 solution | Air | −10.4 | 0 | 35.7 | Nucleation |
| 11 | 2.5 mL of LDH-1 solution | Air | −16.5 | 0 | 35.4 | Nucleation |
| 12 | 2.5 mL of LDH-1 solution | Air | −15.5 | 0 | 36.1 | Nucleation |
| 13 | 2.5 mL of LDH-1 solution | Air | −10.5 | 0 | 43.9 | Nucleation |
| 14 | 2.5 mL of LDH-1 solution | Air | −9.8 | 0 | 24.9 | Nucleation |
| 15 | 2.5 mL of LDH-1 solution | Air | −11.0 | 0 | 39.2 | Nucleation |
| 16 | 2.5 mL of LDH-2 solution | Argon | −3.1 | 14 | 29.9 | Nucleation |
| 17 | 2.5 mL of LDH-2 solution | Argon | −2.9 | 14 | 18.9 | Nucleation |
| 18 | 2.5 mL of LDH-2 solution | Argon | −3.1 | 14 | 23.3 | Nucleation |
| 19 | 2.5 mL of LDH-2 solution | Argon | −2.7 | 14 | 19.6 | Nucleation |
| 20 | 2.5 mL of LDH-2 solution | Argon | −3.1 | 14 | 32.1 | Nucleation |
| 21 | 2.5 mL of LDH-2 solution | Argon | −2.6 | 14 | 35.2 | Nucleation |
| 22 | 2.5 mL of LDH-2 solution | Air | −5.0 | 0 | 38.3 | Nucleation |
| 23 | 2.5 mL of LDH-2 solution | Air | −5.5 | 0 | 40.0 | Nucleation |
| 24 | 2.5 mL of LDH-2 solution | Air | −2.3 | 0 | 36.5 | Nucleation |
| 25 | 2.5 mL of LDH-2 solution | Air | −3.8 | 0 | 42.0 | Nucleation |
| 26 | 2.5 mL of LDH-2 solution | Air | −5.1 | 0 | 50.2 | Nucleation |
| 27 | 2.5 mL of LDH-2 solution | Air | −5.9 | 0 | 40.6 | Nucleation |

It should be noted that the stochastic nucleation temperatures observed for LDH-2 were substantially warmer than the stochastic nucleation temperatures for LDH-1. This difference may be due to some contaminant acting as a nucleating agent in the LDH-2. The stochastic nucleation temperatures are much closer to the controlled nucleation temperatures for LDH-2 compared to LDH-1, yet the improvements in retention of enzyme activity obtained via controlled nucleation for LDH-1 and LDH-2 are similar at 18.1% and 14.8%, respectively. This result suggests that the improvements in retention of enzyme activity can be partially attributed to the characteristics of the controlled nucleation process itself, not just to the prescribed warmer nucleation temperatures obtained via depressurization.

Example 10

Reducing Primary Drying Time

A 5 wt % mannitol solution was prepared by mixing about 10.01 grams of mannitol with about 190.07 grams of water. Vials were filled with 2.5 mL of the 5 wt % mannitol solution. The vials were weighed empty and with the solution to determine the mass of water added to the vials. The twenty vials were placed in a rack on a freeze-dryer shelf in close proximity to one another. The temperatures of six vials were monitored using surface mounted thermocouples; all monitored vials were surrounded by other vials to improve uniformity of vial behavior. The freeze-dryer was pressurized to about 14 psig in a controlled gas atmosphere of argon gas. The freeze-dryer shelf was cooled from room temperature to about −6° C. to obtain vial temperatures of between approximately −1° C. and −2° C. The freeze-dryer was then depressurized from about 14 psig to about atmospheric pressure in less than five seconds to induce nucleation of the solution within the vials. All vials observed visually or monitored via thermocouples nucleated and began freezing immediately after depressurization.

The shelf temperature was then lowered rapidly to about −45° C. to complete the freezing process. Once all vial temperatures were about −40° C. or less, the freeze-drying chamber was evacuated and the process of primary drying (i.e., sublimation) was initiated. During this drying process, the freeze-dryer shelf was warmed to about −14° C. via a one hour ramp and held at that temperature for 16 hours. The condenser was maintained at about −60° C. throughout the drying process. Primary drying was stopped by turning off the vacuum pump and backfilling the chamber with argon to atmospheric pressure. The vials were promptly removed from the freeze-dryer and weighed to determine how much water was lost during the primary drying process.

In a separate experiment as part of Example 10, other vials were filled with 2.5 mL of the same 5 wt % mannitol solution. The vials were weighed empty and with the solution to determine the mass of water added to the vials. The vials were loaded into the freeze-dryer in the same manner described above, and the temperatures of six vials were once again monitored using surface-mounted thermocouples. The freeze-dryer shelf was cooled rapidly from room temperature to about −45° C. to freeze the vials. Nucleation occurred stochastically between about −15° C. and about −18° C. during the cooling step. Once all vials temperatures were about −40° C. or less, the vials were dried in a manner identical to the method described above. Upon conclusion of primary drying, the samples were promptly removed from the freeze-dryer and weighed to determine how much water was lost during the primary drying process.

TABLE 10

Increasing the Nucleation Temperature Improves Primary Drying

| Vial # | Solution | Atmos | Initial Vial Temp. [° C.] | Pressure Drop [psi] | Water Loss [%] | Depressurization Outcome |
|---|---|---|---|---|---|---|
| 1 | 2.5 mL of 5 wt % mannitol | Argon | −1.3 | 14 | 89.9 | Nucleation |
| 2 | 2.5 mL of 5 wt % mannitol | Argon | −1.9 | 14 | 85.2 | Nucleation |
| 3 | 2.5 mL of 5 wt % mannitol | Argon | −1.3 | 14 | 87.1 | Nucleation |
| 4 | 2.5 mL of 5 wt % mannitol | Argon | −2.3 | 14 | 88.8 | Nucleation |
| 5 | 2.5 mL of 5 wt % mannitol | Argon | −2.1 | 14 | 85.0 | Nucleation |
| 6 | 2.5 mL of 5 wt % mannitol | Argon | −1.1 | 14 | 80.7 | Nucleation |
| 7 | 2.5 mL of 5 wt % mannitol | Air | −15.7 | 0 | 65.7 | — |
| 8 | 2.5 mL of 5 wt % mannitol | Air | −16.7 | 0 | 66.9 | — |
| 9 | 2.5 mL of 5 wt % mannitol | Air | −14.5 | 0 | 64.6 | — |
| 10 | 2.5 mL of 5 wt % mannitol | Air | −15.6 | 0 | 64.7 | — |
| 11 | 2.5 mL of 5 wt % mannitol | Air | −16.5 | 0 | 64.1 | — |
| 12 | 2.5 mL of 5 wt % mannitol | Air | −17.9 | 0 | 65.7 | — |

Results of the freeze-drying process with controlled nucleation and stochastic nucleation are summarized in Table 10. It should be noted that these two experiments only differ in the addition of the controlled nucleation via depressurization step to one experiment. As seen in Table 10, the controlled nucleation process achieved via depressurization allows nucleation at very low degrees of sub-cooling, between about −1.1° C. and −2.3° C. in this example. The much warmer nucleation temperatures for the controlled nucleation case compared to the stochastic nucleation case yields an ice structure and resultant lyophilized cake with dramatically improved drying properties. For the same amount of drying time, the vials nucleated using the disclosed depressurization methods between about −1.1° C. and −2.3° C. lost an average of 86.1% of their water while the vials nucleated stochastically between about −14.5° C. and −17.9° C. only lost an average of 65.3%. Hence, the vials nucleated stochastically would require much more primary drying time to achieve the same degree of water loss as the vials nucleated in a controlled manner in accordance with the presently disclosed methods. The improvement in drying time is likely attributed to the formation of larger ice crystals at warmer nucleation temperatures. These larger ice crystals leave behind larger pores upon sublimation, and the larger pores offer less resistance to the flow of water vapor during further sublimation.

Another benefit associated with the above presented temperature quench and pressure induced nucleation control methods is that by controlling the lowest nucleation temperature and/or the precise time of nucleation one can affect the ice crystal structure formed within the frozen vials or containers. The ice crystal structure is a variable that affects various properties of the preserved material, including but not limited to, activity, functionality, and viability as well as the time it takes for ice to sublimate during a freeze-drying process. Thus, controlling the ice crystal structure is important for both cryopreservation and freeze-drying processes.

INDUSTRIAL APPLICABILITY

The present method provides an improved method for controlling the temperature and/or time at which sub-cooled materials, namely liquids or solutions, nucleate and then freeze. Although this application focuses in part on freeze-drying, a similar problem occurs for any material processing step that involves a nucleated phase transition. Examples of such processes include the crystallization of polymers and metals from melts, crystallization of materials from super-saturated solutions, crystallization of proteins, artificial snow production, food freezing, freeze concentration, fractional crystallization, cryo-preservation, or condensation of vapors to liquids.

The most immediate benefit of controlling the nucleation temperature of a liquid or solution is the ability to control the number and size of the solid domains produced by the phase transition. In freezing water, for example, the nucleation temperature directly controls the size and number of ice crystals formed. Generally speaking, the ice crystals are fewer in number and larger in size when the nucleation temperature is warmer.

The ability to control the number and size of the solid domains produced by a phase transition may provide additional benefits. In a freeze-drying process, for example, the number and size of the ice crystals strongly influences the drying properties of the lyophilized cake. Larger ice crystals produced by warmer nucleation temperatures leave behind larger pores upon sublimation, and the larger pores offer less resistance to the flow of water vapor during subsequent sublimation. Hence, the present methods provide a means of increasing primary drying (i.e., sublimation) rates in freeze-drying processes by increasing nucleation temperature.

Another possible benefit may be realized in applications where sensitive materials are preserved via freezing processes (i.e., cryopreserved). For example, a biological material including but not limited to, mammalian tissue samples (e.g., cord blood, tissue biopsy, egg and sperm cells, etc.), cell lines (e.g., mammalian, yeast, prokaryotic, fungal, etc.) and biological molecules (e.g., proteins, DNA, RNA and subclasses thereof) frozen in an aqueous solution may experience various stresses during the freezing process that may impair the function or activity of the material. Ice formation may physically disrupt the material or create severe changes in the interfacial bonding, osmotic forces, solute concentrations, etc. experienced by the material. Since nucleation controls the structure and kinetics of ice formation, it can significantly influence these stresses. The presently disclosed methods therefore provides a unique means of mitigating stresses associated with cryopreservation processes and enhancing the recovery of function or activity from cryopreserved materials. The present methods also represent improvement over conventional nucleation control methods (e.g., seeding or contact with cold surfaces) used to initiate extracellular ice formation in two-step cryopreservation algorithms designed for living cells for small to large commercial scale.

The present methods may be also applied to complex solutions or mixtures containing several constituents both in cryopresevation and lyophilization applications. These formulations are often solutions with an aqueous, organic, or mixed aqueous-organic solvent containing a pharmaceutically active ingredient (e.g., a synthetic chemical, protein, peptide, or vaccine) and optionally, one or more mitigating constituents, including bulking agents that help prevent physical loss of the active ingredient during drying (e.g., dextrose, glucose, glycine, lactose, maltose, mannitol, polyvinyl pyrrolidone, sodium chloride, and sorbitol); buffering agents or toxicity modifiers that help maintain the appropriate environmental pH or toxicity for the active constituent (e.g., acetic acid, benzoic acid, citric acid, hydrochloric acid, lactic acid, maleic acid, phosphoric acid, tartaric acid, and the sodium salts of the aforementioned acids); stabilizing agents that help preserve the structure and function of the active constituent during processing or in its final liquid or dried form (e.g., alanine, dimethylsulfoxide, glycerol, glycine, human serum albumin, polyethylene glycol, lysine, polysorbate, sorbitol, sucrose, and trehalose); agents that modify the glass transition behavior of the formulation (e.g., polyethylene glycol and sugars), and anti-oxidants that protect the active constituent from degradation (e.g., ascorbate, sodium bisulfate, sodium formaldehyde, sodium metabisulfite, sodium sulfite, sulfoxylate, and thioglycerol).

Since nucleation is typically a random process, a plurality of the same material subjected to identical processing conditions might nucleate at different temperatures. As a result, the properties of those materials that depend on nucleation behavior will likely differ despite the identical processing conditions. The disclosed methods provide a means for controlling the nucleation temperatures of a plurality of materials simultaneously and thereby offers a way to increase the uniformity of those product properties that depend on nucleation behavior. In a typical freeze-drying process, for example, the same solution in separate vials may nucleate stochastically over a wide range of temperatures, and as a result, the final freeze-dried products may possess significant variability in critical properties like residual moisture, activity and reconstitution time. By controlling the nucleation temperature via the presently disclosed process, the vial-to-vial uniformity of product properties from a freeze-drying can process can be dramatically improved.

The ability to control the nucleation behavior of a material may also provide substantial benefit in reducing the time necessary to develop an industrial process that hinges upon a normally uncontrolled nucleation event. For example, it often takes many months to develop a successful freeze-drying cycle that can be accomplished in a reasonable amount of time, yields desired product properties within the specified uniformity, and preserves sufficient activity of the active pharmaceutical ingredient (API). By providing a means of controlling nucleation and thereby potentially improving primary drying time, product uniformity, and API activity, the present methods should dramatically reduce the time necessary to develop successful freeze-drying protocols.

In particular, the potential benefits of the present nucleation process provide increased flexibility in specifying the composition of the formulation to be freeze-dried. Since controlled nucleation can better preserve the API during the freezing step, users should be able to minimize the addition of mitigating constituents (e.g., stabilizing agents) to the formulation or chose simpler combinations of formulation constituents to achieve combined stability and processing goals. Synergistic benefits may arise in cases where controlled nucleation minimizes the use of stabilizing agents or other mitigating constituents that inherently lengthen primary drying times (e.g., by decreasing glass transition temperatures of aqueous solutions).

The disclosed methods are particularly well-suited for large scale production or manufacturing operations since it can be conducted using the same equipment and process parameters that can easily be scaled or adapted to manufacture a wide range of products. The process provides for the nucleation of materials using a process where all manipulations can be carried out in a single chamber (e.g., a freeze-dryer) and where the process does not require use of a vacuum, use of additives, vibration, electrofreezing or the like to induce nucleation.

In contrast to the prior art, the present method does not add anything to the lyophilized product. It only requires that the materials, (e.g., liquids in the vials), be held initially at a specified pressure under a gas environment and that the pressure is rapidly reduced to a lower pressure or the temperature is uniformly controlled to induce nucleation. Any applied gas will be removed from the vials during the lyophilization cycle. The vials or their contents are not contacted or touched with anything except the gas. Simple manipulation of the ambient pressure and gas environment or the uniform cryogenic cold gas temperature is sufficient on its own to achieve that goal. By relying only on ambient pressure change to induce nucleation or a temperature change of the uniform cryogenic cold gas, the present method disclosed herein uniformly and simultaneously affects all vials within a freeze-dryer or uniform flow controlled rate freezer.

The present embodiment is also less expensive and easier to implement and maintain than prior art methods of influencing nucleation in materials in lyophilization applications. The present method enables significantly faster primary drying in lyophilization processes, thereby reducing processing costs for freeze-dried pharmaceuticals. The present method produces much more uniform lyophilized products than prior art methods, thereby reducing product losses and creating barriers to entry for processors unable to meet tighter uniformity specifications. This method achieves these benefits without contaminating the lyophilized product. Greater process control should lead to an improved product and shortened process times.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A method of controlling a freezing process comprising:
providing a plurality of containers proximate a porous surface in a cooling chamber, each of the plurality of containers holding a material;
uniformly cooling the material in each of the plurality of containers to a temperature near or below a phase transition temperature while the containers are in the cooling chamber via heat transfer between the material in each of the plurality of containers and a cryogenic cold gas uniformly flowing from the porous surface in a substantially unidirectional orientation and substantially parallel to longitudinal axes of the plurality of containers; and
uniformly performing a temperature quench of the material in each of the plurality of containers by rapidly reducing the temperature of the cryogenic cold gas to initiate and control nucleation of freezing of the material in each of the plurality of containers in the cooling chamber.

2. The method of claim 1, wherein the uniform flow is substantially laminar.

3. The method of claim 1, wherein the plurality of containers comprises at least 10,000 vials and the onset of nucleation of freezing of the material in each of the plurality of vials occurs substantially simultaneously.

4. The method of claim 1, wherein the plurality of containers includes at least 50,000 vials and the onset of nucleation of freezing of the material in each of the plurality of vials occurs substantially simultaneously.

5. The method of claim 1, wherein the plurality of containers comprise a plurality of bags and the onset of nucleation of freezing of the material in each of the plurality of bags occurs substantially simultaneously.

6. The method of claim 1, wherein the material in each of the plurality of containers comprises microorganisms, tissues, organs, live cells, stem cells, primary cells, cell lines, small multicellular organisms, complex cellular structures, live or attenuated viruses, nucleic acids, monoclonal antibodies, polyclonal antibodies, biomolecules, non-peptide analogues, peptides, proteins, RNA, DNA, oligonucleotides, and/or viral particles.

7. The method of claim 1, wherein at least two of the plurality of containers contain different materials.

8. A method of controlling a freezing process comprising:
   providing a plurality of containers proximate a porous surface in a cooling chamber, each of the plurality of containers holding a material;
   uniformly cooling the material in each of the plurality of containers to a temperature near or below a phase transition temperature while the containers are in the cooling chamber via heat transfer between the material in each of the plurality of containers and a cryogenic cold gas uniformly flowing from the porous surface in a substantially unidirectional orientation and substantially parallel to longitudinal axes of the plurality of containers;
   increasing the pressure in the cooling chamber; and
   decreasing the pressure applied to the material in each of the plurality of containers in the cooling chamber to initiate and control the nucleation of freezing of the material in each of the plurality of containers.

9. The method of claim 8, wherein the step of uniformly cooling the material and the step of increasing the pressure in the cooling chamber are performed concurrently.

10. The method of claim 8, wherein the uniform flow is substantially laminar.

11. The method of claim 8, wherein the plurality of containers comprises at least 10,000 vials and the onset of nucleation of freezing of the material in each of the plurality of vials occurs substantially simultaneously.

12. The method of claim 8, wherein the plurality of containers includes at least 50,000 vials and the onset of nucleation of freezing of the material in each of the plurality of vials occurs substantially simultaneously.

13. The method of claim 8, wherein the plurality of containers comprise a plurality of bags and the onset of nucleation of freezing of the material in each of the plurality of bags occurs substantially simultaneously.

14. The method of claim 8, wherein the material in each of the plurality of containers comprises microorganisms, tissues, organs, live cells, stem cells, primary cells, cell lines, small multicellular organisms, complex cellular structures, live or attenuated viruses, nucleic acids, monoclonal antibodies, polyclonal antibodies, biomolecules, non-peptide analogues, peptides, proteins, RNA, DNA, oligonucleotides, and/or viral particles.

15. The method of claim 8, wherein at least two of the plurality of containers contain different materials.

16. The method of claim 8, wherein the pressure is greater than atmospheric pressure prior to decreasing the pressure.

17. The method of claim 8, wherein the pressure decrease is greater than 7 psi.

18. The method of claim 8, wherein the pressure decrease results in a pressure ratio greater than 1.2.

* * * * *